(12) United States Patent
Bond et al.

(10) Patent No.: US 9,193,664 B2
(45) Date of Patent: Nov. 24, 2015

(54) DIRECTED NUCLEATION AND CRYSTAL GROWTH FROM SOLUTION USING SURFACE ENERGY MODIFIED AMORPHOUS MATERIALS

(71) Applicant: DeNovX, LLC, Streamwood, IL (US)

(72) Inventors: Andrew H. Bond, Hoffman Estates, IL (US); Kevin M. Schaab, Spring Valley, CA (US)

(73) Assignee: DENOVX, LLC, Streamwood, IL (US)

( * ) Notice: Subject to any disclaimer, the term of this patent is extended or adjusted under 35 U.S.C. 154(b) by 121 days.

(21) Appl. No.: 14/207,267

(22) Filed: Mar. 12, 2014

(65) Prior Publication Data

US 2014/0275611 A1    Sep. 18, 2014

Related U.S. Application Data

(60) Provisional application No. 61/794,821, filed on Mar. 15, 2013.

(51) Int. Cl.
*B01D 9/00* (2006.01)
*C07C 69/86* (2006.01)
*C07C 67/52* (2006.01)

(52) U.S. Cl.
CPC ............... *C07C 69/86* (2013.01); *C07C 67/52* (2013.01)

(58) Field of Classification Search
CPC .................................. C13K 1/10; B01D 9/00
USPC ...................................................... 23/295 R
See application file for complete search history.

(56) References Cited

U.S. PATENT DOCUMENTS

| 7,122,083 | B2 | 10/2006 | Green |
| 7,763,471 | B2 | 7/2010 | Pamula et al. |
| 2004/0005255 | A1 | 1/2004 | Green |
| 2012/0076860 | A1 | 3/2012 | Trout et al. |
| 2013/0118399 | A1 | 5/2013 | Chadwick et al. |

FOREIGN PATENT DOCUMENTS

| WO | WO-01/90449 | 11/2001 |
| WO | WO-02/101127 | 12/2002 |

OTHER PUBLICATIONS

Aizenberg et al. Control of Crystal Nucleation by Patterned Self-Assembled Monolayers. Nature. 398:495-498 (1999).
Aizenberg. Crystallization in Patterns: a Bio-Inspired Approach. Adv. Materials 16(15):1295-1302 (2004).
Cazabat. Dynamics of wetting: effects of surface roughness. J. Phys. Chem. 90:5845-5849 (1986).
Cox. Controlling the Polymorphism of Active Pharmaceutical Ingredients with Two-Dimensional Templates. Master's Thesis. Worchester Polytechnic Institute. pp. 1-36 (2009).
Croker et al. Mechanistic Features of Polymorphic Transformations. Crys. Growth Des. 10:2806-2816 (2010).
Curcio et al. Probabilistic Aspects of Polymorph Selection by Heterogeneous Nucleation on Microporous Hydrophobic Membrane Surfaces. J. Crystal Growth. 310:5364-5369 (2008).
Diao et al. Gel-Induced Selective Crystallization of Polymorphs. J. Amer. Chem. Soc. 134:673-684 (2011).
Grigorieva et al. Crystallization of Amino Acids on Substrates with Superficial Chiral Reliefs. Mendeleev Commun. 14(4):150-152 (2004).
Grzeisak et al. New Form Dsicovery for the Analgesics Flurbiprofen and Sulindac Facilitated by Polymer-Induced Heteronucleation. J. Pharm. Sci. 96(11):2978-2986 (2007).
Holbrough et al. Topographical Control of Crystal Nucleation. Crys. Growth Des. 12:750-755 (2012).
Lamour et al. Contact Angle Measurements Using a Simplified Experimental Setup. J. Chem. Educ. 87(12):1403-1407 (2010).
PCT/US2014/025089 International Search Report and Written Opinion dated Jul. 3, 2014.

*Primary Examiner* — Edward Johnson
(74) *Attorney, Agent, or Firm* — Wilson Sonsini Goodrich & Rosati

(57) ABSTRACT

A means of directing nucleation and crystal growth has been developed in which these stages of crystallization are influenced by surface energy modifications to amorphous substrates. The surface energy of a substrate can affect the contact angle, line tension, wettability and energetics of the interaction with a supersaturated solution, and these factors are important in crystallization. The use of amorphous substrates creates an opportunity to modify their surface to create useful ranges of surface energies that enhance or inhibit, as may be advantageous, the thermodynamic, kinetic, or a combination of both, factors in nucleation, crystal growth, or crystallization from a supersaturated solution.

20 Claims, 9 Drawing Sheets

US 9,193,664 B2

DIRECTED NUCLEATION AND CRYSTAL GROWTH FROM SOLUTION USING SURFACE ENERGY MODIFIED AMORPHOUS MATERIALS

RELATED APPLICATIONS

This application claims the benefit of U.S. provisional patent application No. 61/794,821 entitled "DIRECTED NUCLEATION AND CRYSTAL GROWTH FROM SOLUTION USING SURFACE ENERGY MODIFIED AMORPHOUS MATERIALS" filed on Mar. 15, 2013, which is incorporated by reference in its entirety.

FIELD OF THE INVENTION

Described herein are devices, compositions, and methods for producing crystalline materials from solution. Devices, compositions, and methods described herein direct nucleation and crystal growth from solution using surface energy modified amorphous materials.

BACKGROUND OF THE INVENTION

The solid phase can exist in a variety of forms ranging from amorphous materials with no long range order to crystalline solids that exhibit a high degree of long range order with consistent interatomic spatial distribution throughout the crystal. The atoms, ions, or molecules in a crystal consistently occupy symmetry related locations throughout a crystalline lattice to give a highly pure solid phase that can be obtained consistently, conveniently, and cost effectively.

The process of crystallization is thermodynamically driven and kinetically controlled, and these observations have important implications. The process of crystallization is separated into two stepwise processes, namely crystal genesis, also referred to as nucleation, which is followed by crystal growth. Described herein are methods of directing nucleation and crystal growth using surface energy modifications to amorphous substrates.

SUMMARY OF THE INVENTION

In one aspect, described herein is a device for generating crystals of a solute from a solution comprising a substrate with an amorphous heterogeneous surface, wherein the amorphous heterogeneous surface:
1) incorporates a pre-formed nucleation site array on the surface of the substrate;
2) is placed in direct contact with a solution comprising the solute to be crystallized under conditions that are static, dynamic, or flow, or combinations thereof; and
3) is chemically resistant to dissolving in the solution.

In some embodiments, the pre-formed nucleation site array on the surface of the substrate comprises an array of indentations, dimples, crenels, ridges, channels, steps, kinks, or terraces, or combinations thereof. As used herein, "crenel" refers to features having acute, obtuse, or right angles, or combinations thereof. As used herein, "dimples" refers to nonangular or rounded features that may be above, or below, or combinations thereof, the plane prescribed by the surrounding surface.

In some embodiments, the amorphous heterogeneous surface incorporating the pre-formed nucleation site array modifies the contact angle, line tension, wettability, or surface energy, or combinations thereof, with a solution as compared to an amorphous heterogeneous surface lacking a nucleation site array.

In some embodiments, the pre-formed nucleation site array is engineered on the surface by means of manual, mechanical, or chemical methods, or combinations thereof, to engrave, etch, mill, imprint, lithograph, or print additively, or combinations thereof, on the surface. As used herein, "print additively" refers to methods that involve the deposition of one or more layers of a material onto a surface as by, for example, three dimensional printing and other related techniques practiced by those familiar in the art.

In some embodiments, the substrate is a material that is chemically resistant to dissolving in the solution. In some embodiments, the substrate comprises polypropylene, polyethylene, polytetrafluoroethylene, polyacrylate, polyacrylamide, polystyrene, divinylbenzene, or vinylbenzene, or combinations thereof. In some embodiments, the substrate is a glass substrate.

In some embodiments, the substrate with the amorphous heterogeneous surface is adhered to a second substrate. In some embodiments, the second substrate is a material that is chemically resistant to dissolving in the solution. In some embodiments, the second substrate comprises the same material as the substrate with the amorphous heterogeneous surface. In some embodiments, the second substrate comprises different material as the substrate with the amorphous heterogeneous surface. In some embodiments, the second substrate comprises polypropylene, polyethylene, polytetrafluoroethylene, polyacrylate, polyacrylamide, polystyrene, divinylbenzene, or vinylbenzene, or combinations thereof. In some embodiments, the second substrate is a glass substrate.

In some embodiments, the substrate with the amorphous heterogeneous surface is adhered to a second substrate. In some embodiments, the second substrate is a material that is chemically resistant to dissolving in the solution. In some embodiments, the second substrate comprises the same material as the substrate with the amorphous heterogeneous surface. In some embodiments, the second substrate comprises different material as the substrate with the amorphous heterogeneous surface In some embodiments, the substrate with the amorphous heterogeneous surface is adhered to a second substrate that does not have an amorphous heterogeneous surface.

In some embodiments, the substrate comprises a means for controlling temperature, or modulating temperature, or combinations thereof.

In some embodiments, the substrate comprises a means for controlling temperature, or modulating temperature, or combinations thereof, that is not exposed to the solution.

In another aspect, described herein is a kit comprising a plurality of substrates for generating crystals of a solute from a solution, wherein each substrate:
1) incorporates a pre-formed nucleation site array on the surface of the substrate;
2) is placed in direct contact with a solution comprising the solute to be crystallized under conditions that are static, dynamic, or flow, or combinations thereof; and
3) is chemically resistant to dissolving in the solution;
and wherein each substrate comprises a pre-formed nucleation site array that is identical to, or differs from, other pre-formed nucleation site arrays in the kit.

In some embodiments of the kit described herein, the pre-formed nucleation site arrays on the surface of the substrates comprise an array of indentations, dimples, crenels, ridges, channels, steps, kinks, or terraces, or combinations thereof. In some embodiments, the surface of the substrates incorporating the pre-formed nucleation site arrays modifies the contact angle, line tension, wettability, or surface energy, or combinations thereof, with a solution as compared to the same surface lacking the pre-formed nucleation site array. In some embodiments, the pre-formed nucleation site array is engineered on the surface by means of manual, mechanical, or chemical methods, or combinations thereof, to engrave, etch, mill, imprint, lithograph, or print additively, or combinations thereof, on the surface. In some embodiments, the substrate is a material that is chemically resistant to dissolving in the solution. In some embodiments, the substrates comprise polypropylene, polyethylene, polytetrafluoroethylene, polyacrylate, polyacrylamide, polystyrene, divinylbenzene, or vinylbenzene, or combinations thereof. In some embodiments, the plurality of substrates are the same. In some embodiments, the plurality of substrates are different. In some embodiments, the substrate is a glass substrate. In some embodiments, each substrate with an amorphous heterogeneous surface is adhered to a second substrate. In some embodiments, the second substrate comprises a plurality of second substrates. In some embodiments, the plurality of second substrates are the same. In some embodiments, the plurality of second substrates are different. In some embodiments, each substrate with an amorphous heterogeneous surface is adhered to a second substrate, wherein the substrates are of the same material. In some embodiments, each substrate with an amorphous heterogeneous surface is adhered to a second substrate, wherein the substrates are of the different materials. In some embodiments, each substrate with an amorphous heterogeneous surface is adhered to a second substrate that does not have an amorphous heterogeneous surface. In some embodiments, the kit comprises a means for controlling temperature, or modulating temperature, or combinations thereof. In some embodiments, the kit comprises a means for controlling temperature, or modulating temperature, or combinations thereof, that is not exposed to the solution. In some embodiments, the plurality of substrates are placed in direct contact with the same solution of the solute. In some embodiments, the plurality of substrates are placed in direct contact with different solutions of the solute.

In yet another aspect, described herein is a process of initiating nucleation of crystals of a solute from a solution of the solute comprising contacting the solution of the solute with a substrate having an amorphous heterogeneous surface, wherein the amorphous heterogeneous surface of the substrate:
  1) incorporates a pre-formed nucleation site array;
  2) is placed in direct contact with a solution comprising the solute to be crystallized under conditions that are static, dynamic, or flow, or combinations thereof; and
  3) is chemically resistant to dissolving in the solution.

In another aspect, described herein is a process for generating crystalline material of a solute from a solution of the solute comprising contacting the solution of the solute with a substrate having an amorphous heterogeneous surface, wherein the amorphous heterogeneous surface of the substrate:
  1) incorporates a pre-formed nucleation site array;
  2) is placed in direct contact with a solution comprising the solute to be crystallized under conditions that are static, dynamic, or flow, or combinations thereof; and
  3) is chemically resistant to dissolving in the solution.

In another aspect, described herein is a process of initiating nucleation of crystals of a solute from a solution of the solute, or for generating crystalline material of a solute from a solution of the solute, or combinations thereof comprising contacting the solution of the solute with a substrate having an amorphous heterogeneous surface, wherein the amorphous heterogeneous surface of the substrate:
  1) incorporates a pre-formed nucleation site array;
  2) is placed in direct contact with a solution comprising the solute to be crystallized under conditions that are static, dynamic, or flow, or combinations thereof; and
  3) is chemically resistant to dissolving in the solution.

In some embodiments, the solution of the solute is, or becomes, supersaturated with the solute.

In some embodiments, the process comprises at least one additional step of heating, cooling, or thermally modulating the substrate and the solution of the solute to a temperature that is different from ambient temperature and then heating, cooling, or thermally modulating the solution of the solute and substrate to give a supersaturated solution at a temperature that is equal to, or different from, ambient temperature.

In some embodiments, the process further comprises isolating crystals that are formed by contact of the surface of the substrate with the solution, from the substrate, or the solution, or combinations thereof.

In some embodiments, the pre-formed nucleation site array comprises an array of indentations, dimples, crenels, ridges, channels, steps, kinks, or terraces, or combinations thereof.

In some embodiments, the amorphous heterogeneous surface incorporating the pre-formed nucleation site array modifies the contact angle, line tension, wettability, or surface energy, or combinations thereof, with the solution as compared to the same surface lacking the pre-formed nucleation site array.

In some embodiments, the pre-formed nucleation site array is engineered on the surface by means of manual, mechanical, or chemical methods, or combinations thereof, to engrave, etch, mill, imprint, lithograph, or print additively, or combinations thereof, on the surface.

In some embodiments, the substrate is a material that is resistant to dissolving in the solution.

In some embodiments, the substrate comprises polypropylene, polyethylene, polytetrafluoroethylene, polyacrylate, polyacrylamide, polystyrene, divinylbenzene, or vinylbenzene, or combinations thereof.

In some embodiments, the substrate is a glass substrate.

In some embodiments, the substrate with the amorphous heterogeneous surface is adhered to a second substrate.

In some embodiments, the substrate with the amorphous heterogeneous surface is adhered to a second substrate that does not have an amorphous heterogeneous surface.

In one aspect, described herein is a process for growing crystals of a solute from a solution of the solute, comprising:
  a) contacting the supersaturated solution of the solute with a substrate having an amorphous heterogeneous surface, wherein the surface of the substrate:
    1) incorporates a pre-formed nucleation site array;
    2) is placed in direct contact with a solution comprising the solute to be crystallized under conditions that are static, dynamic, or flow, or combinations thereof; and
    3) is chemically resistant to dissolving in the solution; and
  b) optionally heating, cooling, or thermally modulating the substrate and the solution of the solute to a temperature that is different from ambient temperature and then heating, cooling, or thermally modulating the solution of the solute and substrate to give a supersaturated solution at a temperature that is equal to, or different from, ambient temperature.

In some embodiments, step b) is performed more than once. In some embodiments, the solution of the solute is, or becomes, supersaturated with the solute.

Also described herein is a crystalline material obtained from any process of crystallization described herein.

In one aspect, described herein is a method for producing a crystallization topography comprising incorporating a pre-formed nucleation site array on the surface of a substrate.

In some embodiments, the substrate is a material that is chemically resistant to dissolving in the solution from which crystallization occurs. In some embodiments, the substrate comprises polypropylene, polyethylene, polytetrafluoroethylene, polyacrylate, polyacrylamide, polystyrene, divinylbenzene, or vinylbenzene, or combinations thereof. In some embodiments, the substrate is a glass substrate. In some embodiments, the pre-formed nucleation site array on the surface of the substrate comprises an array of indentations, dimples, crenels, ridges, channels, steps, kinks, or terraces, or combinations thereof. In some embodiments, the surface of the substrate incorporating the pre-formed nucleation site arrays modifies the contact angle, line tension, wettability, or surface energy, or combinations thereof, with a solution as compared to the same surface that lacks the pre-formed nucleation site array. In some embodiments, the pre-formed nucleation site array is engineered on the surface of the substrate by manual, mechanical, or chemical methods, or combinations thereof, to engrave, etch, mill, imprint, lithograph, or print additively, or combinations thereof, on the surface.

Other features and advantages of the invention described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
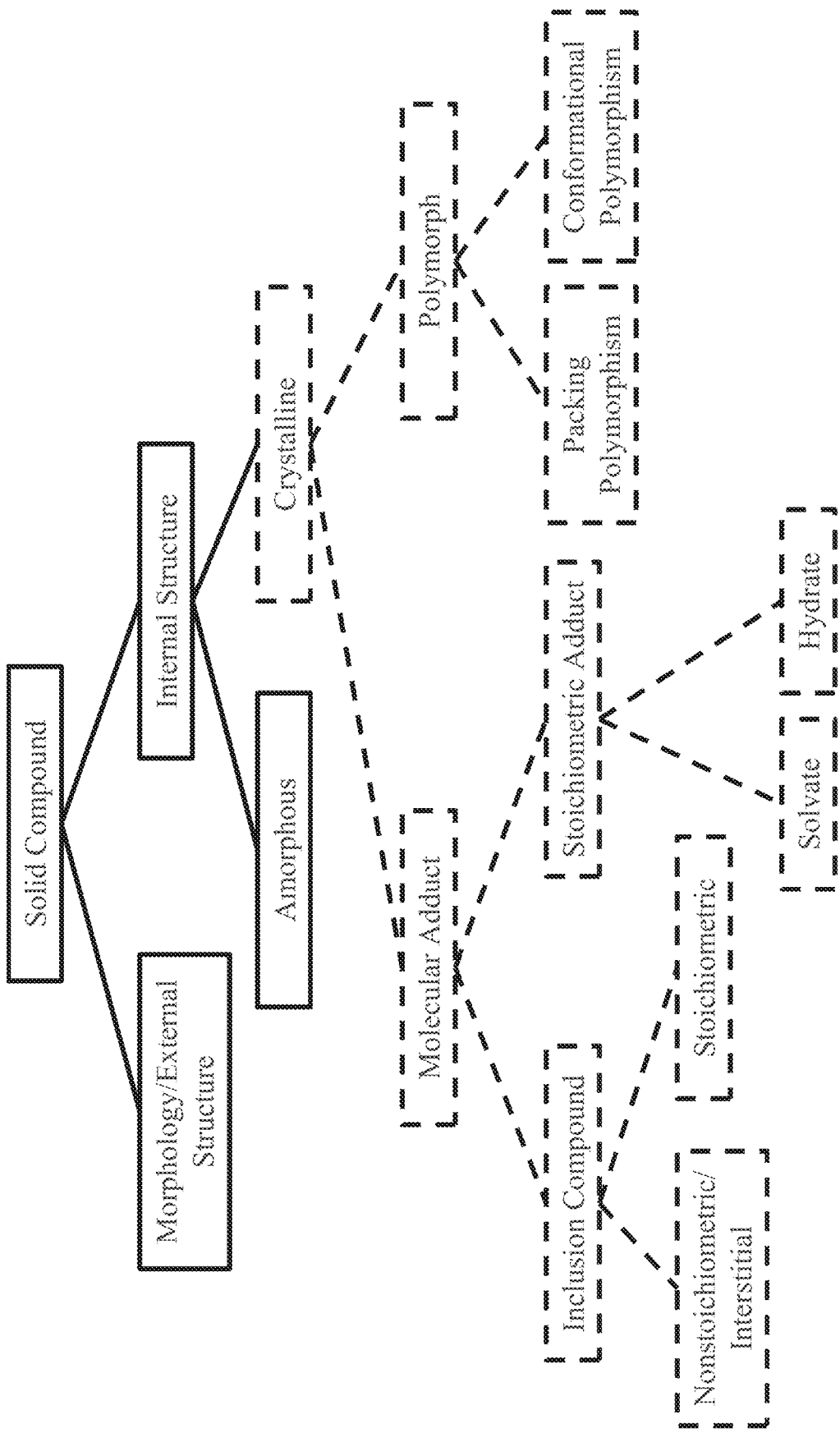
FIG. 1 Possible solid form variants for a single solid material.

The solid phase can exist in a variety of forms ranging from amorphous materials with no long range order to crystalline solids that exhibit a high degree of long range order with consistent interatomic spatial distribution throughout the crystal. The atoms, ions, or molecules in a crystal consistently occupy symmetry related locations throughout a crystalline lattice to give a highly pure solid phase that can be obtained consistently, conveniently, and cost effectively.

Many important physicochemical properties derive from the consistent long range order in crystalline materials, and these include properties that are important in both production and use:
1 Molar Volume
2 Density
3 Index of refraction
4 Color
5 Thermal and electrical conductivity
6 Heat capacity
7 Melting and sublimation temperatures
8 Equilibrium solubility
9 Dissolution rate
10 Propensity of solvate or hydrate formation
11 Chemical reactivity
12 Stability of crystalline solid
13 Physical stability (e.g., hardness, brittleness, compressibility, etc.)
14 Morphology
15 Crystal size distribution
16 Ease of processing The consistent long range order in crystalline materials gives predictable chemical behavior that is commercially important, with applications in the food, pharmaceutical, cosmetic, agricultural, fine chemicals, and bioengineering fields. Each of these application areas demands a high purity material with consistent performance, especially where human usage is involved. Crystalline materials are well suited for applications having regulated purity and performance requirements due to the ease of product recovery from multicomponent process streams, the high purity that is often afforded in a single separative operation, the scalability of the crystallization process itself, and favorable process economics. From an end use perspective, crystalline materials are stable during long term storage and they frequently have reproducible thermodynamic and kinetic properties.

The crystallization process is an operationally and economically preferred technique that has long been exploited due to the consistent properties exhibited by crystalline materials. It is important to separate the reproducible and predictable behavior of crystalline materials from the crystallization process itself, as the latter surprisingly involves several key steps for which the mechanistic understanding still remains poorly understood and inherently unpredictable. The predictable behavior of crystalline materials is so valuable in commercial activities that the underlying lack of understanding about the earliest stages of the crystallization process itself is frequently overlooked until a problem arises.

While a given crystal containing any combination of atoms, ions, or molecules will exhibit consistent long range order, different crystal forms with identical or slightly different chemical compositions can exist and can form at any time. The generic phenomenon is referred to as solid form variation, and as solid form variants when referring to a specific group including a chemical entity of interest. Amongst solid form variants there are several different classifications, with polymorphism rigorously defined as the existence of more than one crystalline form of a given chemical composition whose constituents occupy different locations in the lattice. When the conformation, orientation, or location of an atom or ion in the lattice is different for two crystals of identical chemical composition, the unit cell packing is different and the result is a new polymorph, and conformational polymorphism is a common occurrence for molecules having a high degree of flexibility.

The presence of a solvent molecule in the interstices of the lattice; that is, solvent that does not interact with the chemical entity of interest, yields an inclusion compound and such solid form variants are fragile as loss of solvent can occur easily to give a change in crystal form. When the crystal form changes by addition of a solvent molecule that interacts directly with the atoms, ions, or molecules of interest, a solvate or molecular adduct is formed that is comparatively more stable to solvent loss than inclusion compounds. These solvated species, together with polymorphs, are collectively referred to herein as solid form variants.

From the foregoing, various phases can exist for a solid material and FIG. 1 communicates in part the complexities that arise from solid form variation. By example, complex organic compounds frequently give rise to packing polymorphism or conformational polymorphism, and these different crystal forms can appear at virtually any part of the development and manufacturing processes. Where adduct formation occurs, the intentional or unintentional inclusion of solvent or other molecules can yield many different possibilities, some intentionally designed to improve select properties of a given crystal (e.g., the so called co-crystals), while others may give variants as a result of fortuitous incorporation of impurities, residual solvent, or other components originating from synthesis or production activities. Despite the consistent internal structure exhibited by crystalline materials, FIG. 1 shows that numerous solid form variants can exist, and such variability is a complicating and unpredictable facet of the manufacturing processes that rely on crystallization as a separative technique.

The effects of solid form variation on the 16 physical chemical properties mentioned previously can be significant; for example, consider the different properties, uses, and values of diamond and graphite as two solid form variants of elemental carbon. More broadly, the food, pharmaceutical, cosmetic, agricultural, fine chemical, and bioengineering fields place a special emphasis on select end use properties of crystalline materials. More specifically, commercial use in these fields generally involves a regulated product having both initial and final purity standards, shelf storage prior to usage, and predictable end use performance. The active pharmaceutical ingredients (APIs) used in medicines can be taken as an illustrative example, in which the in vivo equilibrium solubility of the API is of critical importance in usage. Because different solid form variants can have different properties, including vastly different equilibrium solubilities and dissolution rates, the US and international healthcare regulatory bodies enforce strict guidelines to ensure consistent usage characteristics for pharmaceutical products. Critically important properties for APIs include high initial purity, crystal size distribution, shelf stability of solid, physical stability during administration, crystal dissolution rates, and overall ease of manufacturing. Many of these properties exhibit interdependencies (e.g., a broad crystal size distribution can give a broad range of dissolution rates), which are further complicated by the very different end use conditions: pharmaceuticals in human or animal usage, agricultural applications in different geochemical environments, or bioengineering uses that may involve the enhancement or inhibition of biofilm formation.

Underscoring the complexity and breadth of issues arising from solid form variation are those publicized commercial experiences in which products were negatively impacted by solid form variation after human usage of a specific API solid form had been approved by regulatory authorities. The cautionary tale of Abbott Laboratories' Ritonavir product (marketed as Norvir®) has been widely used as the preferred case study in polymorphism and its commercial implications. Ritonavir is a 98 atom organic molecule for HIV treatment and it proceeded successfully through clinical trials and received regulatory approval for human use as a liquid gel. Approximately two years after commercial launch, a batch of Ritonavir capsules failed a regulated dissolution test due to the emergence of a slower to dissolve, and previously unknown, polymorph. Worldwide availability of Ritonavir was jeopardized and institutional inventories were quarantined during this time because the drug was forming a different crystalline structure which made it less soluble, so the correct dose of drug was not released inside the patient's body.

A focused reformulation effort including new pharmacokinetics studies, production changes, quality control revisions, storage requirements, and resubmission to the various regulatory authorities was required and was completed in approximately 12 months at substantial expense. It is estimated that lost sales alone exceeded $125 million, which does not account for the redevelopment costs and goodwill impairment stemming from damage to the Ritonavir and Abbott Laboratories' brands.

One factor that complicates crystallization as a separation and purification technique is the diversity of the chemical entities that are used in food, pharmaceutical, cosmetic, agricultural, fine chemical, and bioengineering applications. The classes of chemical entities can range from atoms and low molecular weight ions to complex organic molecules and macromolecules capable of different conformational arrangements and complex intermolecular interactions. The molecular weight spectrum of APIs alone can span from the small molecule to the biological macromolecular range, with the latter often predisposed to conformational polymorphism and solvation-based solid form variation. The very different uptake, targeting, and therapeutic mechanisms of APIs often require different chemical functionalization, and this can impact conformation, intramolecular interactions, intermolecular interactions, and solvate formation in the crystal.

Current pharmaceutical research and development most frequently involves the preparation, production, and usage of the salt forms of APIs and, more specifically, that the API contain an ionizable functionality that is charge neutralized by a biologically acceptable counterion. The advantages of salt formation for APIs are numerous and include the unification of certain in vivo behaviors even for very different classes of API molecules. In addition, the introduction of an ionizable functionality, commonly carboxylic acid groups, can facilitate isolation of the API as a crystalline material with the resulting advantages that span synthesis and isolation to in vivo usage. Where in vivo use is the objective, salt formation can improve water solubility of the API that produces benefits from production through to pharmacokinetics.

After salt formation, the isolation of a crystalline solid simplifies purification and handling, and for a given API there is reduced susceptibility to reaction during shelf storage of either the intermediate or final product. Crystalline APIs are also preferred as they facilitate use in tablets and capsules, which dominate the various pharmaceutical administration methods. As a result of these studies, nearly 50% of all APIs in use today are produced as salt forms to impart water solubility and so that the materials can be isolated as crystalline solids with the concomitant production, usage, and economic advantages.

Despite the numerous and important advantages of salt formation to a variety of developmental and commercial uses, salt formation ultimately increases the probability of solid form variation. The use of salt co-ions can give rise to itinerant structural behavior in which different intra- or intermolecular interactions arise between respective cations and anions (e.g., bridging interactions, bifurcated interactions, etc.). The introduction of a salt forming functionality also increases the molecular complexity of the molecule and can increase the probability of solid form variation. The presence of polarized ionic moieties also increases the propensity of hydrate and solvate formation, which can lead to a variety of potential variations (FIG. 1) and can impact shelf stability, solubility, and dissolution rates.

Even optimized crystallization processes can be negatively affected by solid form variation. By example, the use of seed crystals in research, development, and production activities is a common practice. As the seeds become increasingly purified after repeated recrystallization from one batch to the next, the increasing purity can shift the equilibrium and system energetics to give a new solid form variant. From an operational perspective, business trends involving multiple API development and production facilities in wide ranging geographic regions with different personnel and different environmental conditions introduce many nonreproducible variables. These factors collectively reduce the predictability of a crystallization operation; however, they are present day standard practices that require the development of new and improved crystallization methods.

Underscoring the pervasiveness of solid form variation in commercially relevant activities, it is reported that: " . . . polymorphism is a widespread phenomenon observed in more than half of all drug substances . . . " and that: "Polymorphism and pseudopolymorphism are known to influence every stage in the manufacture and storage of pharmaceuticals." (Stahl, P. H.; Wermuth, C. G. *Handbook of Pharmaceutical Salts: Properties, Selection, and Use*. Wiley-VCH: New York, 2002).

Given the intensely regulated nature of pharmaceutical production and usage, the decisions surrounding which crystalline salt form of an API to move forward to synthesis scale-up, pharmacokinetic studies, clinical trials, and into the market is so important as to have been described as "irreversible": "The present-day situation of industrial drug development makes the salt-decision an almost irreversible one, because a change of the salt form during the later stages of the development of a drug candidate entails high additional expenses and loss of valuable time . . . " (Stahl, P. H.; Wermuth, C. G. *Handbook of Pharmaceutical Salts: Properties, Selection, and Use*. Wiley-VCH: New York, 2002).

Thus, the benefits of a highly pure crystalline API that exhibits consistent chemical behavior over its product lifetime have been broadly acknowledged and are now regulated from drug candidate development through to commercial usage. This model and the associated regulations, however, are subject to the inherent lack of predictability posed by solid form variation, and the already observable increases in this phenomenon are predicted to grow as a result of the current developmental strategies that favor salt formation and the ever increasing complexity of the API molecules used in medicine. This divergence from predictability suggests that new methods for crystallization are needed to improve both chemical and economic predictability, and that any such improvements must be accommodative of the increasing diversity of chemical entities that are, or will be, commercially used in food, pharmaceutical, cosmetic, agricultural, fine chemical, and bioengineering applications.

Despite empirical study for over a century and recently expanded interest in crystal design, the primary treatises on commercially relevant crystallization processes still concede that many practitioners still treat crystallization as an art.

With the current state of crystallization technology still consistently referred to in the scientific literature as an "art", it is clear that new, rational methods of identifying and controlling solid form variation are needed. New capabilities enabling faster and easier solid form screening purport to facilitate the identification of polymorphs, solvates, and other solid form variants before they advance to production and, ideally, before they enter the marketplace where end use hazards and public safety issues arise. This approach to solid form screening employs a combinatorial high throughput philosophy that lacks the economic and technical advantages of a rational methodology. Many combinatorial approaches are not mass efficient and require comparatively large quantities of an experimental material (which is typically in short supply) to be distributed across tens of thousands of wells with different chemical conditions, making recovery nearly impossible. A rational screening approach will have lower mass requirements, be more efficient with the material that is available, and will permit more target compounds to enter pharmacodynamic testing at an earlier stage by reducing the early stage synthesis burden. Of nearly equal importance, new rational crystallization methods that are applicable to diverse chemical species are necessary, as the ever increasingly complex nature of food, pharmaceutical, cosmetic, agricultural, fine chemical, and bioengineering products will likely give rise to more solid form variation.

New crystallization methods are also needed from a business perspective, as rational techniques that can make production more predictable, scalable, and cost effective are economically advantageous. Rational crystallization methods must also address the disparate conditions of discovery and production activities, as more variables avail themselves at the laboratory scale while economic, engineering, and regulatory constraints limit the range of variables practical at the production scale. New crystallization tools must be durable and useful under various laboratory conditions:

1 Different chemical entities (e.g., atoms, ions, molecules) and chemical classes
2 Different solvents
3 Temperatures
4 Pressures (for evaporation)
5 Reactants to reduce solubility
6 Versatile experimental form factors
   a Vessels
   b Surfaces incorporated into a container wall
   c Surfaces adhered to a container wall
   d Suspended module in contact with solution
   e Freely floating module in contact with a solution
   f Any of the above means in intermittent contact with a solution At the production-scale numerous operational limitations arise and more engineering and economic oriented factors become important:

1 Physical durability
2 Chemical stability
3 Stability under shear conditions
4 Versatile form factors
   a Vessels
   b Surfaces incorporated into a container wall
   c Surfaces adhered to a container wall
   d Suspended module in contact with solution
   e Freely floating module in contact with a solution
   f Any of the above means in intermittent contact with a solution The requirements that new, rational crystallization methods accommodate diverse chemistries across vastly different scales for products with different end use requirements is a significant challenge that is addressed within the scope of the subject invention.

Current theories describing the crystallization process rely on the premise that crystallization is essentially a molecular recognition process occurring on a grand scale.

In this context, molecular recognition is defined herein to include recognition of all relevant chemical species to include atoms, ions, molecules, and biological macromolecules. In its simplest form, molecular recognition can be envisaged as deposition of molecules in an orderly way onto a lattice. Only those molecules that a good fit are deposited onto the lattice surface.

The consistent long range order of a crystal derives from the aforementioned molecular recognition and self assembly processes, in which solutes with favorable energetics are transferred into and through a phase boundary while impurities are rejected. An understanding of the mechanism and role of this recognition process in crystallization is important, as it is difficult to recreate universal recognition capabilities for diverse chemical classes of solutes-yet recognition is necessary to producing crystalline materials.

The process of crystallization is thermodynamically driven and kinetically controlled, and these observations have important implications. In systems that give crystalline solids comparatively quickly, rarely is the first obtained crystal form the most thermodynamically stable structure. In many cases, including noteworthy examples involving Abbott's Ritonavir product, the crystalline materials initially obtained and administered to patients were kinetically controlled products and were not the thermodynamically stable crystalline materials. In such cases, the kinetically controlled product has sufficient chemical potential to drive the various equilibria towards its formation and such a condition can inhibit isolation of the thermodynamically stable form. Only after some change in system variables is encountered, such as an unexpected difference in cooling rate as a result of a plant-scale transfer, exposure to different particulate contaminants (whether airborne or residual in equipment), aging of the solution, etc., does the thermodynamically stable crystal structure appear.

Because different thermodynamic and kinetic drivers impact the crystallization process at different stages, the process of crystallization is separated into two stepwise processes. Crystal genesis is referred to as nucleation, in which species of interest first aggregate, either from the melt or from solution, while remaining soluble in the liquid phase. Upon reaching a system dependent critical size, the aggregate undergoes further self organization to form a parent, or seed, crystal. After nucleation, the parent crystal enters the second stage, termed crystal growth, and subsequently progresses from a microcrystalline seed to a macrocrystalline solid by the addition of the species of interest to the different faces of the crystal. As a result of the highly organized structure of crystalline solids and the ease with which they are studied, the prevailing theories frequently extrapolate backwards and rely on models involving an orderly and systematic addition of individual species to give stepwise nucleation and crystal growth models.

Nucleation is an important first step in the crystallization process, and it is an attractive starting point for the development of new and improved crystallization methods. Protein crystal structures are pivotal to the success of rational drug design and other biotechnology applications; however, obtaining high quality crystals poses a major problem to progress. Nucleation is recognized as the first step that affects the remainder of the crystallization process, thus control of nucleation would solve many problems with crystallization at its conception.

Nucleation occurs by two principal mechanisms: primary nucleation and secondary nucleation. The former, by definition, occurs in the absence of crystalline surfaces, whereas secondary nucleation requires the presence of some crystalline surface around which aggregation and growth occurs. In the absence of crystalline surfaces, primary nucleation may occur by homogeneous or heterogeneous pathways. Homogeneous primary nucleation is a spontaneous event in which the solute aggregates themselves achieve the critical size needed for nucleation, and it is quite rare outside the laboratory and virtually impossible to observe at the process-scale given the variety of materials intentionally and unintentionally in contact with a supersaturated solution in commercial production facilities. Heterogeneous primary nucleation involves the presence of foreign matter, such as particulates or chemical species (e.g., solvent, additives, impurities, etc.) that serve to lower the energy barrier to nucleation. Given the ubiquity of particulate contaminants in even the most carefully controlled laboratory and Certified Good Manufacturing Facility (cGMP) environments, heterogeneous primary nucleation is the most frequently encountered of the primary nucleation mechanisms.

The presence of a particulate contaminant, suspended solids, dust, or a chemical impurity can lower the system energetics to give aggregates of the critical size needed for nucleation. In particulate contaminated systems, nucleation can occur at lower levels of supersaturation, and studies have shown that heterogeneous primary nucleation is more common in systems where the contaminant size and structure closely resembles that of the species to be crystallized. Research has shown that the structural disparity between the contaminant and the target chemical entity must be less than 15% for there to be an energetic advantage, and this observation means that structurally similar chemical byproducts or process contaminants can adversely impact crystallization processes.

While "engineered foreign matter" may initially appear promising as a means of inducing heterogeneous primary nucleation at lower supersaturation ratios, the interactions of such "foreign matter" with a growing solute aggregate prior to nucleation is unpredictable. In the context of cGMP production of regulated food, pharmaceutical, cosmetic, and related products, such unpredictable behavior is not acceptable.

Secondary nucleation involves a parent crystalline surface present in solution, and it is intermittently used in laboratory crystallizations that involve a previously isolated seed crystal used to induce nucleation. At larger scales, seed crystals can be introduced by a reserve or "holdback" in the reactor vessel of a portion of a prior crystallization run. Process-scale crystallizations also involve mechanical agitation that can lead to microcrystalline fragmentation, or "collision breeding", under shear conditions to produce fragments that are dispersed and can serve as nucleation centers. While poorly understood, several stages of secondary nucleation have been postulated:

1 Generation of microcrystalline fragments from the parent crystal by mechanical agitation causing crystals to collide with other crystals, with the container, or with the mixing apparatus 2 Dispersion of the microcrystalline fragments into the bulk medium by mixing or diffusion 3 Solute aggregation around the microcrystalline fragment to yield aggregates with the critical size needed for nucleation Secondary nucleation using seed crystals of the parent compound under high shear conditions can be convenient, but it is not universally applicable: suitable parent seed crystals do not exist for most new chemical entities. The strategy of secondary nucleation by seeding is limiting in the discovery phase of a new chemical entity where seed crystals are not yet available or may be difficult to isolate. Further, use of seed crystals in production activities requires expensive large scale empirical calibration of the shear conditions and, more importantly, secondary nucleation can still yield kinetically controlled products rather than the desired thermodynamically stable crystal form. Secondary nucleation by crystal seeding also suffers from unpredictable behavior as seed stocks can undergo gradual purification as a result of repeated recrystallizations, which can lead to an increased probability of solid form variation as trace solution components (e.g., impurities, particulates, etc.) are gradually reduced and new crystallization conditions unintentionally emerge. Given these limitations, the emphasis of the subject invention is on heterogeneous primary nucleation.

Supersaturation is the driving force for nucleation, and it occurs when the solute concentration in solution exceeds the equilibrium solute solubility determined under ideal thermodynamic conditions. The supersaturation ratio is an important component of the theoretical framework for nucleation, and is defined as:

$$S = \frac{C}{C_0} \qquad \text{Eqn. 1}$$

where C is the solute concentration in the supersaturated solution and $C_0$ is the thermodynamic solubility limit.

Supersaturation is a nonideal, metastable thermodynamic state in which minute perturbations can lead to significant changes that may include formation of amorphous precipitates or crystalline solids. The metastable state of supersaturation frequently rests near an energetic inflection point, where a shallow energetic well of stability may exist for a system containing solute at a concentration exceeding its thermodynamic equilibrium value, and the activation energy barrier for exiting such a metastable state can be quite small and can correspond to minor perturbations to the system. The size and shape of the metastable zone is related to the supersaturation ratio of a solution, wherein higher supersaturation actually decreases metastability and lower supersaturation has a comparatively larger metastable region.

There are four principal means of manipulating supersaturation, and these include:
1 Temperature change
2 Solvent evaporation
3 Changes to the solvent composition to reduce solute solubility
4 Chemical reaction These four methods are convenient for laboratory-scale crystallization, but most process-scale operations emphasize thermal and evaporative techniques, as they do not require the addition of chemicals that would involve additional costs and downstream processing. The laboratory- and process-scales also utilize different levels of supersaturation. Laboratory-scale crystallizations generally focus on isolation for analysis of a new chemical entity, and these studies are typically performed at low supersaturation because limited quantities of the new chemical entity are available at the developmental stage. Process-scale crystallization most frequently targets purity, yield, and overall process efficiency, such that intermediate levels of supersaturation are employed. Crystallization operations performed at very high levels of supersaturation are less common because of the decreased metastability of the solution, making it susceptible to dramatic changes (e.g., amorphous precipitation, monolith formation, runaway thermal event, etc.) that give undesirable product qualities.

A metastable supersaturated solution relies on nucleation to reduce the system free energy, thereby permitting a return to an equilibrium condition. Prior to nucleation, the solute in a supersaturated solution becomes concentrated enough to yield intermolecular aggregates or clusters, and this aggregation represents the first stage of the recognition process as applied to crystallization. Aggregates form in solution in order to maximize favorable solvation effects, minimize unfavorable solvation effects, optimize intermolecular interactions, and to reduce the overall system free energy. As part of the aggregation process, solutes coalesce and thermodynamically undesirable species are excluded from the fluxional solution phase structure, with the result being a first step in the dynamic recognition process that evolves through the nucleation and crystal growth stages. One readily observable result of aggregation is the increased viscosity that generally accompanies increases in supersaturation, where the solution viscosity can increase dramatically as a result of solute aggregation. Viscosity changes are more pronounced for supersaturated solutions than for undersaturated solutions, and column sedimentation experiments using supersaturated salt solutions have reported aggregate concentration gradients that were used in preliminary cluster size calculations.

Examination of the thermodynamic drivers for homogeneous primary nucleation provides a simplified, instructive basis for understanding heterogeneous primary nucleation and permits a sensitivity analysis with respect to the practically important variables. Homogeneous primary nucleation of an idealized spherical aggregate involves the difference between the positive free energy required for formation of the nucleus surface in a supersaturated solution and the negative free energy change for the phase transformation (i.e., aggregate nucleus in solution transitioning to a microscopic crystal):

$$\Delta G = 4\pi r^2 \sigma + \frac{4}{3}\pi r^3 \Delta G_v \qquad \text{Eqn. 2}$$

where r is the radius of an ideal spherical solute aggregate, $\sigma$ is the surface tension, and $\Delta G_v$ is the free energy change for the phase transformation.

The first term is a "nucleation resistor" and corresponds to the free energy required to form the nucleus surface in a microdomain of the supersaturated solution, and this energetic barrier is presented by the cohesive surface tension forces of the supersaturated solution that resist rearrangement and displacement as the subcritical nucleus forms. The second term involving $\Delta G_v$ represents the favorable energetics of the phase transformation and corresponds to a system energy decrease as the metastable state is exited and crystallization begins.

By minimizing $\Delta G$ in Eqn. 2 with respect to the aggregate radius r and introducing the Gibbs-Thompson equation for aggregate growth, a critical free energy for nucleation can be obtained:

$$\Delta G_{cr} = \frac{16\pi \sigma^3 v^2}{3(kT \ln S)^2} \qquad \text{Eqn. 3}$$

where v is the molecular volume, T the system temperature, and S the supersaturation ratio from Eqn. 1.

For aggregates smaller than the critical size needed for nucleation, solute diffusion away from the cluster is thermodynamically preferred. Beyond a solute- and system-dependent critical aggregate size; however, $\Delta G_{cr}$ trends negative and spontaneous aggregate growth occurs. It is this step, where solute addition by an aggregate becomes thermodynamically favored and the critical free energy of nucleation is achieved, that occurs near the energetic inflection point in a metastable system. Phrased differently, supersaturated solutions are metastable because a critically-sized aggregate is needed to alleviate the nonequilibrium supersaturation condition.

The point at which the aggregate achieves the critical size for solute addition to become thermodynamically favorable is highly dependent on the chemical properties of the solute, the supersaturated solution, and on the macroscopic conditions. Equations 2 and 3 show that the free energy favoring aggregate formation and growth to a critical size is dependent on a number of variables including the specific volume of the solute and the aggregate radius, both of which are largely molecule- and system-dependent values and their manipulation is only practical in phenomenological laboratory studies and not in commercial research or production activities. The two most conveniently manipulated variables for process-scale crystallizations are the supersaturation ratio and system temperature, and these are optimized whenever possible. Practical limits to these controls do exist, as nucleation and crystal growth kinetics can be adversely impacted by a high supersaturation ratio that reduces the metastability of the system and can lead to poor crystal size distribution, undesirable morphology, reduced purity levels, and to isolation of the kinetically controlled product rather than the preferred thermodynamically stable product. As a result of the complex interdependence between temperature and supersaturation ratio and the nonequilibrium condition of the supersaturated state, an empirical approach is generally required to obtain a useful understanding of how these variables affect a given crystallization system. Such an empirical approach is mass intensive, and not well suited to the discovery phase of development or to research or production activities involving biological macromolecules and proteins that are temperature sensitive and can frequently exhibit itinerant solubility as a function of temperature.

The remaining variable that appears in both Eqn. 2 and Eqn. 3 is the interfacial tension, or surface energy, and its importance to the crystallization process has been acknowledged along with the difficulty in harnessing its utility.

In current practice the interfacial surface tension, or surface energy, can be modified by judicious solvent selection; however, production operations, regulatory guidelines, and process economics frequently mandate that the solvent system be aqueous, especially in food, pharmaceutical, cosmetic, agricultural, and bioengineering processing where purity standards are the most stringent.

Given that supersaturated solutions require formation of a suitably sized aggregate to relieve the nonequilibrium metastable condition and that surface energies are an important aspect of aggregate formation and growth, the convenient and predictable manipulation of surface energies in supersaturated solutions would be of utility. It is the manipulation of the solute aggregates before, during, and after the nucleation process by surface energy modification that is one important aspect of the subject invention.

Recalling that crystallization is a thermodynamically driven process that is kinetically controlled, an understanding of the time components are warranted. Substituting Eqn. 3 into an Arrhenius type rate equation, where A and $B_0$ are rate related, and solving for k gives:

$$k = \left[\frac{-16\sigma^3 v^2}{3 \ln\left(\frac{B_0}{A}\right)T^3(\ln S)^2}\right]^{\frac{1}{3}} \qquad \text{Eqn. 4}$$

The format of Eqn. 4 shows comparable cubic magnitudes between σ (a nucleation resistor) and T (typically a nucleation enhancer). Increasing S also enhances and accelerates nucleation, but it can dramatically reduce the metastability of the system by causing many nuclei to form with an adverse effect on related end use properties, of which crystal size distribution is one example. Further complicating a sensitivity analysis is the itinerant behavior of solute solubility as a function of temperature for different species; for example, proteins and other macromolecules may exhibit decreasing solubility as temperature increases while many small molecules, simple ions, and the like typically exhibit increasing solubility with a temperature increase. Equation 4 also predicts that above a critical supersaturation there should be exponential growth; however, in practice there exists a temperature at which the solution becomes too viscous to nucleate. This rate decrease as a function of viscosity is related to the surface energy term, in that formation of a new surface in the highly viscous supersaturated solution is energetically challenged, and Eqn. 5 has been successfully applied to an aqueous supersaturated solution of citric acid:

$$B_0 = A \exp\left[\frac{-16\pi\sigma^3 v^2}{3k^3 T^3(\ln S)^2} + \frac{\Delta G_{visc}}{kT}\right] \qquad \text{Eqn. 5}$$

The second term involving $G_{visc}$ is increasingly important at higher supersaturation levels and after a system dependent critical supercooling temperature is achieved, and it causes nucleation rates to decrease due to viscosity limited diffusion that precludes new surface formation for nucleating species. As with the thermodynamics, the kinetic drivers also exhibit complex interdependencies and are limited to certain system regimes, which collectively limit the utility and predictability of current crystallization methods.

Technological improvements to nucleation and crystal growth must be compatible with existing production methods and crystallization processes in order to be commercially deployed. A key objective of crystallization is the efficient recovery of a highly purified product, and any addition of modifiers to alter the course of crystallization is rigorously debated and generally disfavored by pharmaceutical and food-related practitioners and their regulatory oversight authorities. In order to maximize utility and facilitate adoption, additions to a process stream should be generally be avoided and, where unavoidable, added constituents should be immobile with respect to the product effluent or easily recovered by macroscopic physical methods as described in the subject invention. The contact of a supersaturated solution with a macroscopic surface to facilitate rational heterogeneous primary nucleation is an interesting approach. The ability to control such a process (i.e., nucleation) lies at the heart of the development of a novel technology or microstructure. This is because nucleation controls to a large extent the initial structure, type, size, scale and spatial distribution of the product phases.

Figure 2:
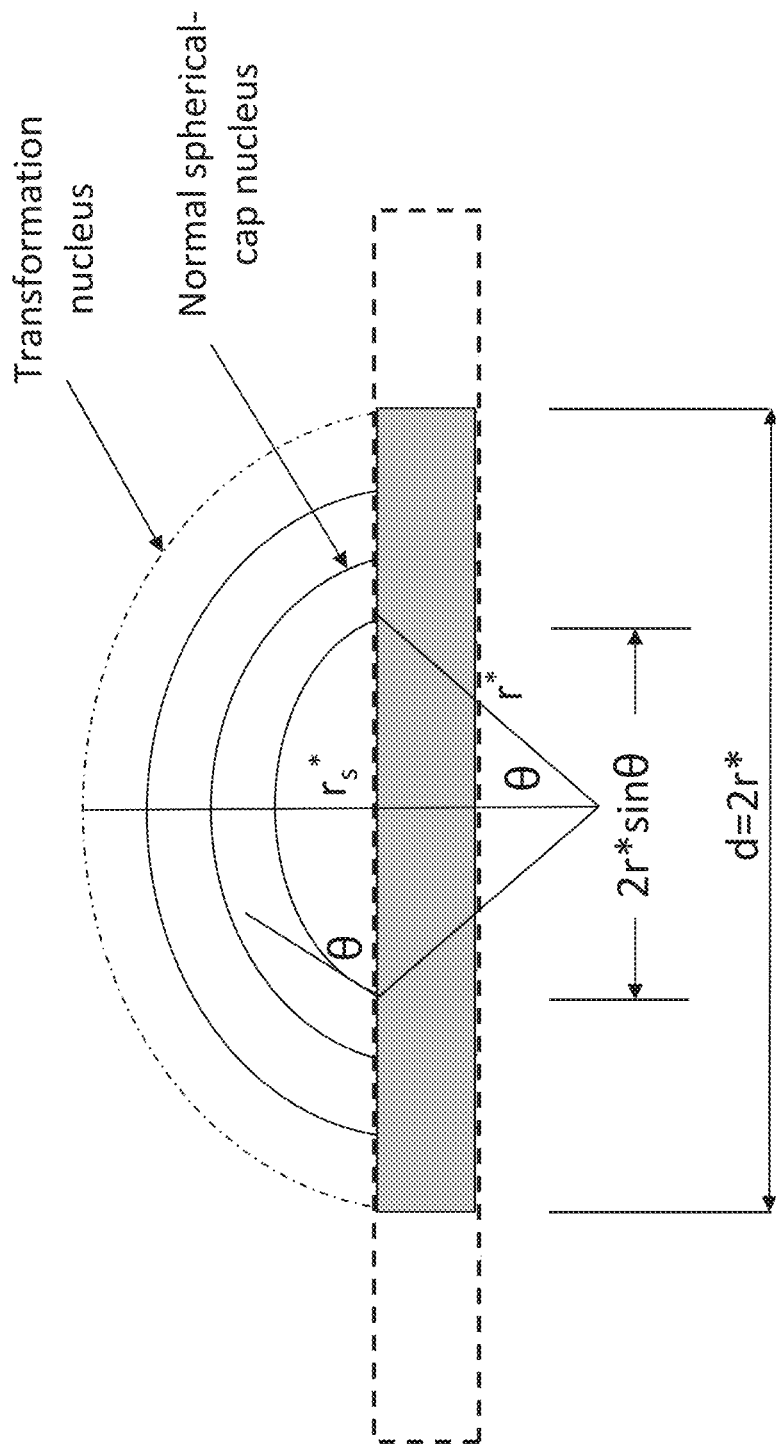
FIG. 2. Flat surface theoretical model for nucleation showing the size requirements for the Transformation Nucleus.

The theory of nucleation on a surface describes an orderly, stepwise mechanism involving adsorption of individual solutes onto a surface, diffusion of those solutes along the surface, and nucleation subsequently occurs when the coalesced solutes achieve the system dependent critical size and $G_{cr}$ from Eqn. 3 trends negative to favor spontaneous growth. This mechanistic perspective is oversimplified and ignores the role of solute self aggregation, the addition of individual solute molecules to aggregates in solution, the coalescence of aggregates, and the addition of aggregates to heterogeneous surfaces in solution. Given the supersaturated concentration regime and the fluxional nature of solution structures, it is feasible that the nucleation process can include processes that derive from individual solute behavior, from solute aggregates, and from a combination of these solution phase species. The differences in chemical behavior and the physical properties of individual solute molecules and aggregates of these species are well documented, and the underlying role of a nucleation surface can be summarized for convenient discussion. A surface facilitating, or inhibiting, nucleation can impact the energy barrier to nucleation in a number of ways:

1. Providing a structurally similar template lattice as in epitaxial methods, including liquid phase epitaxy
2. Stabilizing an intermediate structure between that of the solute aggregates in solution and the crystal structure
3. Excluding or removing solvent impurities from the aggregate structure prior to nucleation
4. Facilitating the formation of intermolecular (or interatomic) interactions that stabilize the growing aggregate and the crystal structure
5. Facilitating coalescence of adjacent solute aggregate clusters to achieve the critical size needed for spontaneous growth The theoretical treatises on heterogeneous nucleation on a substrate take a geometrical perspective, with the underlying premise that the substrate surface geometry can impact the nucleation process. The boundary extremes of this theory include the flat surface model and the spherical model, with the former depicted in FIG. 2. The theoretical description of nucleation on a flat substrate gives a "transformation nucleus" (FIG. 2); that is, an aggregate of adequate size that $G_{cr}$ trends negative leading to nucleation. In this Turnbull model, nucleation on a surface occurs for those aggregates where the substrate dimensions are $>2r^*$ ($r^*$ is the critical radius for nucleation) and for which the aggregate radius is $>2r^*\sin\theta$, as shown in FIG. 2.

Figure 3:
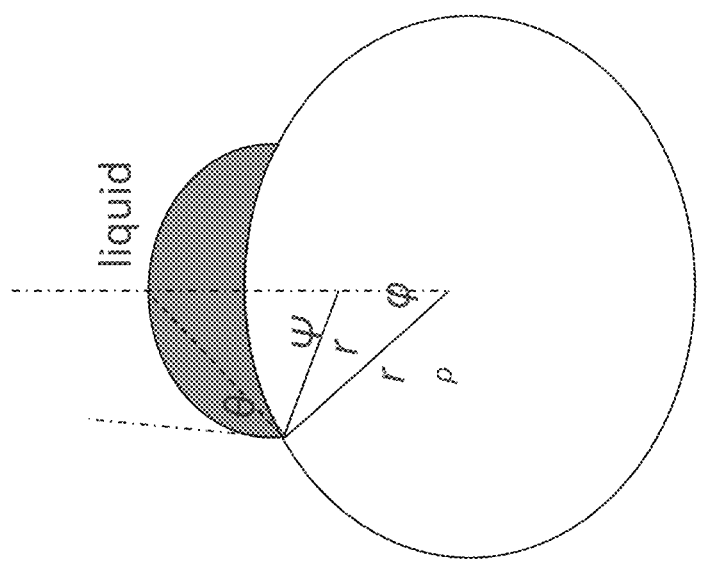
FIG. 3. Cap shaped nucleus forming on a convex surface from which the shape factor f(m,x) of Eqn. 6 is derived.

Migrating from the flat surface to a different theoretical boundary comprising the convex spherical substrate shown in FIG. 3, a new term involving the shape factor $f(m,x)$ can be derived to give Eqn. 6:

$$f(m,x) = 1 + \left(\frac{1-mx}{g}\right)^3 + x^3\left(2 - 3\left(\frac{x-m}{g}\right) + \left(\frac{x-m}{g}\right)^3\right) + 3mx^2\left(\frac{x-m}{g} - 1\right) \qquad \text{Eqn. 6}$$

Incorporating this $f(m,x)$ shape factor into an equation for the free energy of nucleation gives the Fletcher model of Eqn. 7:

$$\Delta G^* = 8\pi\sigma/3(\Delta G_v)^2 f(m,x) \qquad \text{Eqn. 7}$$

The Fletcher model predicts that the shape factor, $f(m,x)$, decreases with increasing substrate radius, such that large spherical substrates may provide more thermodynamically favorable conditions for nucleation (i.e., $f(m,x)$ decreases and reduces the system energy as shown in Eqn. 7).

From an energetic perspective, an idealized heterogeneous nucleation event for a cap shaped liquid sample of a supersaturated solution on either a spherical substrate or a flat substrate essentially give identical cluster radius requirements. More importantly, the critical free energy required for nucleation is reduced on a heterogeneous substrate compared to homogeneous nucleation in solution, Eqn. 8:

$$\Delta G^*_{het} = \frac{1}{2}\Delta G^*_{hom} \qquad \text{Eqn. 8}$$

The importance of Eqn. 8 can be appreciated by recognizing that a lower energy requirement means that nucleation on a heterogeneous surface can occur at lower levels of supersaturation, and this observation has been historically attributed to the presence of "foreign substances" in the supersaturated solution. Given the continuum of surface features between flat, spherical, and convex, useful opportunities for improving nucleation processes exist and a host of substrate materials can be engineered to accommodate such features, or combinations thereof.

Figure 4:
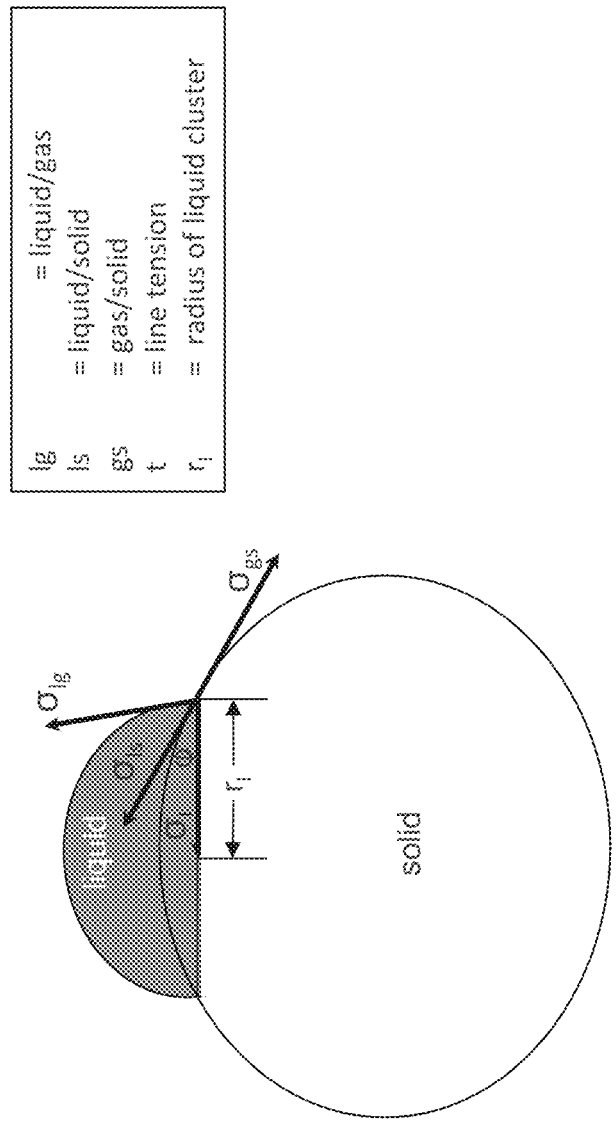
FIG. 4. Cap shaped liquid on a convex surface showing the interfacial tangents used in line tension.

For a liquid droplet on a surface, the solid, liquid, and gas phases converge to yield a three phase interfacial line as shown in FIG. 4. The macroscopic contact angle, defined as $\sigma_t$ in FIG. 4, yields important information relating to the wettability of the substrate in contact with the drop, and by minimizing the line tension, the overall energetic barrier to nucleation can be reduced. The unifying theme in the discussion of nucleation on surfaces is the favorable thermodynamic effect that a heterogeneous substrate surface can have on aggregate coalescence and growth in a supersaturated solution to give a nucleation event.

The kinetics of nucleation on a surface can be described using a modified Arrhenius relationship, and accounting for line tension corrections, any increase in the line tension will accelerate the nucleation rate on a substrate surface and a likewise decrease in line tension will reduce the overall substrate induced nucleation rate.

The inverse relationship between the effect of line tension on nucleation thermodynamics (where decreasing line tension reduces the free energy of nucleation) and nucleation kinetics (where decreasing line tension decreases the nucleation rate) is an important point. This generalized relationship is also in keeping with Ostwald's rule stating that the first obtained crystal is seldom the thermodynamically stable product, rather it is the kinetically favored product. As such, a careful balance between nucleation and crystal growth thermodynamics, kinetics, and operational requirements of production activities must be established.

The identification and isolation of the thermodynamically stable crystalline material is an important commercial objective of crystallization, and this is particularly so in the heavily regulated food, pharmaceutical, cosmetic, agricultural, fine chemical, and bioengineering fields. To meet these needs, new nucleation methods are needed to facilitate the formation and isolation of the most thermodynamically stable crystal forms as early in the development process as possible. To this end, some understanding of the interdependence between nucleation and crystal growth is needed.

Crystal growth commences immediately after an aggregate achieves the critical size needed for nucleation and the thermodynamics of solute retention become energetically favorable. Numerous observations have indicated that the thermodynamic and kinetic aspects of crystal growth are enhanced by surface heterogeneities, collectively referred to as "surface roughness" on the crystalline substrate. This observation can be mechanistically rationalized using the "nearest neighbor" effect, in which an increase in interactions with adjacent, similar species yields a favorable thermodynamic effect.

From a kinetic perspective, increased surface heterogeneity reduces the surface diffusion distances between favorable interactions and thus faster nucleation and crystal growth rates may be observed.

After the aggregate has matured through nucleation to the crystal growth phase, the prevailing theories suggest four fundamental locations, or surface heterogeneities, where adsorbed solutes can be incorporated into a growing crystal: terraces, steps or step faces, kinks, and screw dislocations. These four fundamental features are used in descriptions of crystal growth that rely on convenient one-at-a-time mechanisms of solute addition that are derived by working backwards from the known crystal structure to arrive at a mechanism for growth in solution. Further complicating this stepwise description is the fact that terraces, steps, kinks, and screw dislocations are transitory: as growth proceeds (by any mechanism) the features are dynamic in structure and in location and should not be viewed from a static perspective. Such bias is unintentional, but nonetheless imposes constraints on the mechanism of nucleation and crystal growth that need not be limiting. Expanding the fundamental mechanisms to include growth of subcritical nuclei and of crystal growth itself by both solute aggregate addition as well as one-solute-at-a-time growth may create new options for improving the nucleation and crystal growth processes. The various dynamic surface heterogeneities described here can impact the surface energy of a growing solute aggregate as shown in Equations 3, 7, and 8, and such surface features are important in designing new approaches to nucleation and crystal growth.

Most discussions present stepwise processes for crystal growth that include the adsorption of a solute onto a crystal surface, solute diffusion along a terrace, and then incorporation into the growing crystal at a site of heterogeneity (i.e., a step face, kink, or screw dislocation) that increases the nearest neighbor interactions and provides a thermodynamically favorable environment. A number of models attempt to explain the kinetics of crystal growth (e.g., the BCF theory) using conceptually straightforward mechanisms, but such models are important only for crystals grown by vapor deposition and, in very rare cases, for solution crystallization at very low supersaturation where the crystal/solution interface is quiescent, and where solute/solvent interactions are minimal. Such conditions are encountered infrequently in the laboratory and very rarely at the process-scale, thus limiting the applicability of such models.

A more widely applicable diffusion mechanism capable of accommodating the mixing conditions typical of laboratory and process-scale crystallization has been developed. In contact with solution, a growing crystal creates a solute concentration gradient as the solute of interest is removed from solution and incorporated into the crystal (or aggregate prior to nucleation). The solution layer in contact with the crystal surface is progressively depleted of solute and a concentration gradient with the bulk solution is created. This region is referred to as the "concentration boundary layer" or more commonly the "surface diffusion layer". It is this concentration gradient and the physicochemical properties of the surface diffusion layer that are the foundation of the Diffusion Layer Model, which is generally applicable to both small and large scale crystallization systems that involve mixing.

The Diffusion Layer Model accounts for different surface diffusion layer heights under variable mixing conditions, and it is the diffusion of a solute from the bulk through this surface diffusion layer that is the rate determining step in this model. Solute diffusion in the surface diffusion layer and the height of the boundary layer have been demonstrated to affect crystal growth rates. The surface diffusion layer can alternatively be viewed as a layer of aggregated solutes surrounding a growing crystal, and it is this layer, already rich in aggregated solutes, that is involved in the recognition process.

Two important physical characteristics deriving from crystal growth kinetics are particle size distribution and crystal morphology. Because there is a surface area component to the dissolution of solids, the size and shape of the dissolving crystalline materials are carefully monitored in commercial use and are intensely regulated properties for APIs. By example, crystal size and morphology are important in food-related applications where mouth feel can be a success metric, in cosmetics where skin feel or exfoliation properties are desirable, and in agricultural products where time dependent dissolution may be advantageous. Given that crystal growth is dependent on nucleation, it is well established that the nucleation process and conditions of nucleation can dramatically affect crystal size distribution and morphology: properties from the crystal growth stage that are important to end usage. Acknowledging the importance of this interdependence, new nucleation techniques must account for changes to crystal growth that may ultimately impact end use properties.

When crystallization is described as a "molecular recognition process", severe constraints are imposed on new techniques because of the chemical diversity of solutes for which crystallization is the preferred method of separation, purification, recovery, or any combination thereof. The broad range of solids comprised of atoms, ions, small molecules, biological macromolecules, or their combinations creates an enormous challenge to the utility of new nucleation methods, as it is probable that there is no single nucleation method that will be universally successful across such diverse chemical species. This chemical diversity and the general lack of adequate tools for rationally inducing, inhibiting, or otherwise controlling nucleation explain the predominance of the current empirically-based approaches to solid form screening that rely heavily on trial and error experimentation, combinatorial chemistry, and increasingly on combinatorial high throughput screening methods.

Epitaxial methods have long been promoted as tools for rational crystallization; however, there are fundamental underlying issues with epitaxial methods that limit their utility with respect to new chemical entities. Epitaxy involves a secondary nucleation mechanism that relies on a previously formed crystalline surface to support crystal growth. Unfortunately, the structure of a given epitaxial surface may not be an appropriate structural or energetic match for a new chemical entity, and knowing which epitaxial surface to employ when attempting to crystallize a new chemical entity is presently unknowable. Such structural and energetic mismatches could suppress crystallization entirely, or they could lead to isolation of a kinetically controlled product rather than the preferred thermodynamically stable crystal.

In energetic terms, epitaxial surfaces present to a supersaturated solution a crystal face that has a narrowly defined surface energy, and that energetic regime may not be an appropriate match to facilitate crystallization from solution. In theory, the epitaxial surface is intended to serve as both the recognition and assembly driver for the target system, but the unknown solution behavior and the unknown solid state structure of a new chemical entity combine to make it impossible to select an appropriate epitaxial surface a priori. This fundamental limitation combined with the diversity in chemical behaviors for which crystallization is important severely limit the utility of epitaxial methods in chemical discovery activities.

Accounting for the challenges imposed by the diversity of chemical of species to be crystallized, the subject invention facilitates the coalescence of solutes and solute aggregates to improve nucleation using surfaces that can present a comparably diverse set of surface energies. This strategy leaves the critically important recognition and assembly processes to the respective solutes and their aggregates, rather than trying to substitute recognition and assembly with a preexisting lattice as is the objective of epitaxy and its derivatives. The approach of the subject invention is in keeping with the observations that recognition occurs at the solute aggregate surface prior to nucleation and at the aggregated solute surface diffusion layer of the Diffusion Layer Model of a growing crystal. Rather than surrogating the recognition and assembly process of a new chemical entity and forcing it into an energetic regime narrowly prescribed by an existing epitaxial lattice, the subject invention uses an amorphous surface with suitably modified surface features to present an energy spectrum to solutes and solute aggregates in a supersaturated solution to facilitate aggregate coalescence, growth, and nucleation. Broad utility is achieved not by surrogating the recognition processes important to nucleation and crystal growth, but by leaving these processes to the solutes and their aggregates, and in so doing improving the overall probability of isolating the thermodynamically stable crystalline forms of new chemical entities.

It is the matching of the surface energy of the solute and solute aggregates at an interface with a heterogeneous substrate that presents the best means of improving nucleation processes while maintaining utility across diverse chemical species.

Crystallization is important in numerous commercial activities, spanning research and development to production in the food, pharmaceutical cosmetic, agricultural, fine chemical, and bioengineering industries. As a process, crystallization is valued for its reliability in terms of scalable production and consistent end use product behavior, and from these factors comes predictable cost effectiveness. Solid form variation in all its forms (FIG. 1), and particularly polymorphism, present significant challenges to research and development and process-scale crystallizations, and the resulting lack of predictability introduced by solid form variation can have very costly consequences as evidenced by Abbott's Ritonavir pharmaceutical polymorphism problem. The consequences of solid form variation and contaminant induced heterogeneous primary nucleation reduce the predictability of a crystallization process and can subsequently reduce or eliminate technological and business advantages. Of the two stages of crystallization, nucleation represents the best opportunity to rationally influence outcomes as the fluxional solute aggregates can be rationally predisposed to nucleation using amorphous heterogeneous substrates with engineered surface energy modifications that do not adversely affect the recognition and assembly processes that are vital to nucleation and crystal growth.

As discussed herein, a reduction in the free energy of nucleation on a heterogeneous surface is advantageous compared to homogeneous nucleation. Use of a heterogeneous surface provides an opportunity for rational design of new nucleation systems and for the rational control of nucleation and the subsequent crystal growth step. Engineered heterogeneous surfaces with various features that impart different surface energies can be envisioned.

Contemporary theories and attempts at crystal design frequently rely on epitaxial methods that are based on the use of a crystalline template to enforce ordering of the target solutes at the interface with the supersaturated solution. In theory and in practice, the epitaxial template may or may not be chemically related to the target solute. In terms of nucleation mechanisms, current strategies for crystal design rely on secondary nucleation where a chemically related crystalline template is used as a surface onto which individual solutes adsorb and are assembled under the energetic influence of the underlying lattice. Such methods have been demonstrated for select systems in the laboratory and they see commercial usage in electronics fabrication, where crystallization from the vapor phase is common practice. The broad use of such epitaxy-style growth for crystallization from solution continues to incur numerous challenges, and the limitations of secondary nucleation as applied to discovery phase research involving new chemical entities has been discussed herein.

To be useful, an epitaxial template must present an energetically favorable surface to the solute and the respective aggregates such that there is a near match between the lattice energy of the epitaxial template and the surface energy of the aggregated solutes. More specifically, there must be a close match between the attachment energy, $E_{att}$, of the epitaxial surface and the surface energy of the target solute aggregate, as defined by Eqn. 9:

$$E_{latt} = E_{sl} + E_{att} \qquad \text{Eqn. 9}$$

where:
$E_{latt}$=the lattice energy of the crystal
$E_{sl}$=the slice energy for assembly of a slice or fragment of the crystal
$E_{att}$=the attachment energy released when a slice attaches to the growing crystal For a given crystal form of an arbitrary solute, $E_{latt}$ is a constant and $E_{sl}$ is characteristic for the aggregation of said solute to form a "slice" (i.e., an aggregate surface) in a given solution under a given set of conditions. Thus, Eqn. 9 indicates that the attachment energy for an arbitrary solute, $E_{att}$, is a narrowly defined value and that an epitaxial template must have an energy nearly matching $E_{att}$ in order to exhibit an energetic advantage. This narrow energy window is further supported by the earlier discussion of heterogeneous primary nucleation in which a contaminant surface must closely resemble the size and structure of the target solute with a disparity of no greater than 15% in order for there to be an energetic advantage in the nucleation process. For most research and development projects involving new chemical entities, the lattice energy is not empirically known and the slice and attachment energies are also unknown; thus, predictive capabilities for identifying suitable epitaxial surface templates remain limited.

Numerous reasons for the lack of broad application of epitaxial methods have been discussed, but a major fundamental hurdle is the energetic mismatch between the surface of the crystalline epitaxial template and the $E_{att}$ of the target solute aggregate surface. The lattice presented by an epitaxial template is energetically tuned to such a narrow class of compounds that its utility is concurrently narrow. Thus, new methods are needed that can be more broadly tuned to the $E_{att}$ of diverse classes of chemical species, including, but not limited to, those atoms, ions, and molecules of use in the food, pharmaceutical, cosmetic, agricultural, fine chemical, and bioengineering industries.

The subject invention uses rationally modified amorphous heterogeneous substrates with surface nucleation sites that are varied with respect to nucleation site density, spatial orientation, shape, size, height, and combinations thereof, to improve the thermodynamics, kinetics, purity, morphology, crystal size distribution, ease of processing, or economics of solution crystallization processes. By focusing on the surface energetic properties of solutes and their aggregates in a supersaturated solution and with judicious tuning of the surface energy spectrum by choice of the amorphous substrate materials, nucleation site configurations, and manufacturing methods, the subject invention is broadly applicable to a wide range of solutes as might be encountered in food, pharmaceutical, cosmetic, agricultural, fine chemical and bioengineering uses. The amorphous character, resistance to dissolution, durability, and commodity nature of the preferred amorphous substrate surfaces overcomes the challenges faced by epitaxial-based secondary nucleation methods in solution crystallization. Further, some degree of spatial variation can be introduced into the amorphous heterogeneous substrate nucleation site array, such that the surface energy can accommodate the energetic drivers of a given chemical system rather than enforcing a pre-existing rigid structural and energetic motif (i.e., lattice) onto a system of known or unknown behavior. This rational approach to improving nucleation thermodynamics and kinetics using energy tuned surfaces comprising amorphous substrates and the resultant utility in predisposing solute aggregates to nucleation and crystal growth is a novel approach to improving crystallization and the properties, including but not limited to, morphology, crystal size distribution, ease of processing, handling, and process economics.

Suitably modified amorphous materials are promising as nucleation substrates for numerous reasons that include energetic, chemical, production, and economic factors. The importance of surface energetics has already been discussed herein, as have the limitations of epitaxial and other secondary nucleation methods that rely on surface attachment and narrowly defined values of $E_{att}$. Amorphous materials by definition lack long range order and thus do not have narrowly defined attachment energies; therefore, amorphous materials do not impose a narrow energetic regime on a new chemical entity that may be seeking a different, lower energy state during the nucleation, crystal growth, or phase change processes. By using amorphous substrates modified to present an energy spectrum (suitably engineered for narrow or wide ranges), the $E_{att}$ value is allowed to vary with the new chemical entity thereby improving the probability of achieving a match for $E_{att}$ that is representative of the thermodynamically favorable crystal form for the new chemical entity.

Amorphous materials are very well suited to surface modifications to alter and improve a variety of physical characteristics including wettability and surface contact angles. The wettability, and more accurately contact angle, are related to the surface energy, and the thermodynamics and kinetics of the nucleation process have been demonstrated to be dependent on surface energy interactions.

Figure 5:
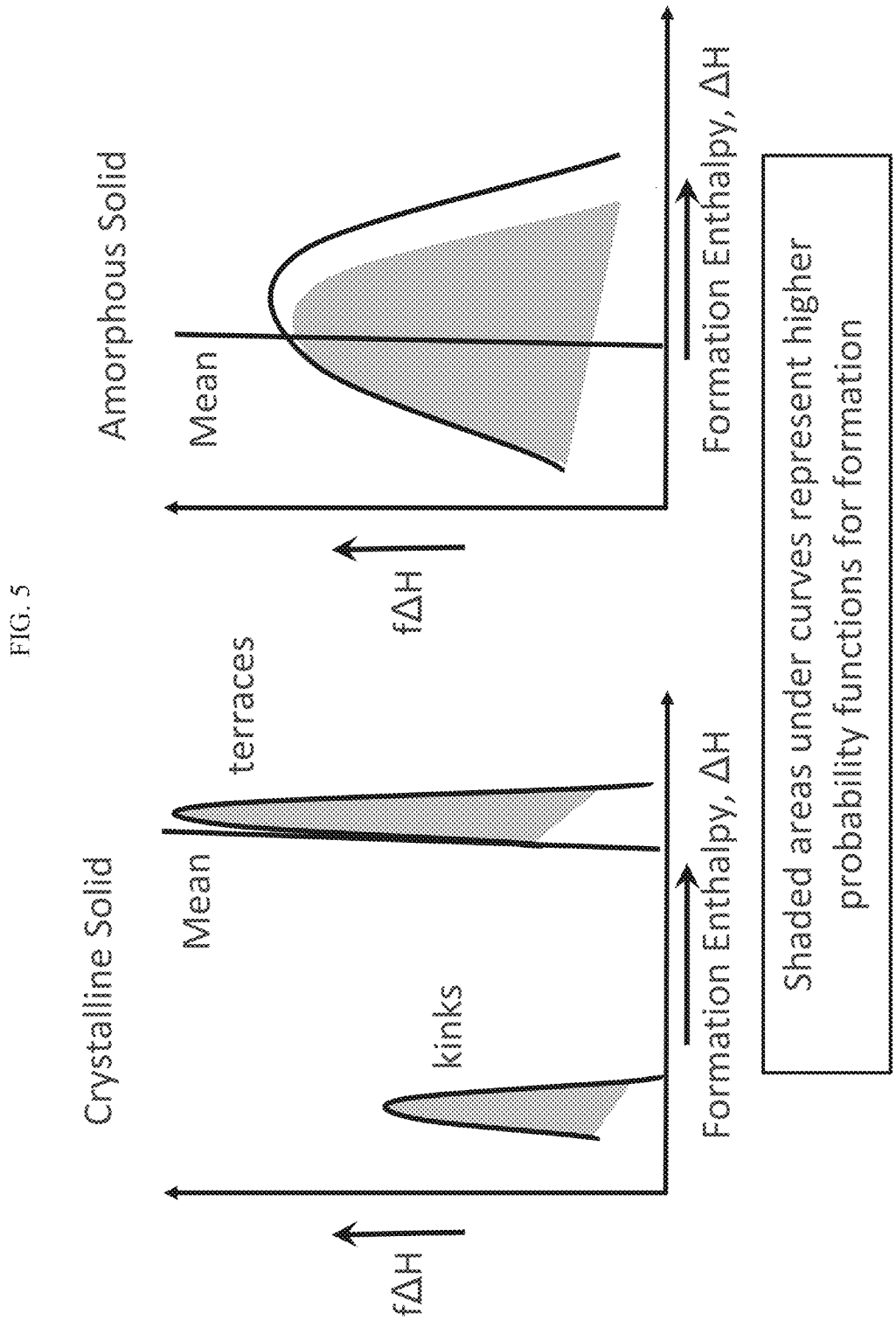
FIG. 5. Nucleation probabilities on crystalline solid substrates and amorphous solid substrates.

Examination of the enthalpy distributions and probability functions for various solids shows that amorphous surfaces (silicon in this case) have higher probabilities of nucleation, as shown graphically in FIG. 5. The left side of FIG. 5 shows narrow shaded peaks representing the nucleation probability functions for the kink and terrace growth features of crystalline solids. These peaks graphically depict the narrow energy range of values for $E_{att}$ for a crystalline surface, and it is this narrow energy spectrum that limits the overall utility of secondary nucleation methods, which includes epitaxy-like techniques. At the right of FIG. 5, amorphous materials exhibit more broad nucleation probability profiles, and the more broad energy range depicted by the shaded region covers a larger area of the enthalpy profile and thus amorphous surfaces provide a higher probability of initiating nucleation events. The rational manipulation of the surface features of amorphous materials to create a suitably broad surface energy spectrum to improve the probability of solute and aggregate coalescence in a supersaturated solution to improve nucleation thermodynamics, kinetics, or both, is one important aspect of this invention.

Amorphous substrates are well suited to surface energy modification and important physical properties can be affected. One surface feature important to interfacial interactions between the supersaturated solution and the substrate is surface wettability. The role of wettability in nucleation is not well understood as some chemical species may interact strongly with a substrate as part of the nucleation process, while others may exhibit itinerant behavior. The dynamic nature of the aggregation, recognition, assembly, nucleation, and crystal growth processes has yet to be fully reflected in the mechanistic descriptions of the underlying processes, in which a short lived, weak interaction may be adequate to overcome the shallow energetic barrier of the metastable state to induce nucleation and to relieve the supersaturated condition.

Extending beyond surface wettability, the three phase line tension (FIG. 4) can also be altered by adjusting the surface energy of an amorphous material. The role of the line tension in nucleation is not yet of utility in a predictive capacity, and attempting to optimize crystallization conditions using line tensions alone remains challenging at the time of writing.

Various surface features can be introduced to an amorphous substrate to alter the surface energetics, and these include:
  1 Nucleation site density
  2 Nucleation site spatial orientation
  3 Nucleation site size
  4 Nucleation size shape
  5 Channels
  6 Concave surfaces
  7 Convex surfaces Various other surface heterogeneities of utility in improving nucleation can be envisioned by those familiar in the art, and this list is not intended to be limiting in any way.

The surface density of nucleation sites is one important and conveniently controlled surface modification, as the uniform two dimensional spacing of nucleation sites on an amorphous heterogeneous substrate can dramatically alter interactions of the surface with the solution, solute, and solute aggregates. Based on crystal growth theories, it has been suggested that a more heterogeneous surface may likewise be of benefit in nucleation processes. At the other extreme, a dramatic reduction in nucleation site density would position nucleation sites so remotely that interactions with adjacent aggregates and adsorbed solutes would be minimized. In this extreme, the thermodynamic advantage deriving from proximity of the solutes and solute aggregates would be diminished.

In the continuum of nucleation site densities between the very high and very low extremes, there are densities that can accommodate diverse system energetics that derive from solute chemistry, solute aggregation characteristics, the physicochemical properties of the contemplated supersaturated solution, the $E_{att}$ of the target solute, and the like. By suitably varying the surface energy of amorphous materials through the use of surface motif variation, enhanced heterogeneous nucleation can be achieved.

Numerous means permit surface modification of amorphous materials to facilitate heterogeneous primary nucleation, and these include the standard manual, mechanical, or chemical methods of engraving and etching, including laser, plasma, and other energy deposition methods. Various lithographic, stamping, imprinting, and additive printing processes avail themselves to motif deposition, and many surface modification techniques deriving from nanotechnology will be also be of utility as recognized by those familiar in the art.

More specifically, the present invention contemplates rationally designed interactions between suitably modified amorphous substrates with solute aggregates in a supersaturated solution to promote heterogeneous primary nucleation. By acknowledging the benefits of surface heterogeneity in nucleation and crystal growth (e.g., step, kink, and screw growth mechanisms), an amorphous substrate presenting appropriately engineered surface energies can be used to influence nucleation processes. Because reproducibility is an important aspect of research, development, and production activities, the amorphous surfaces contemplated herein can be modified in a consistent manner using computer numerically controlled manufacturing methods. In this way, a suitable modification giving a specific range of surface energies can be consistently manufactured to give reproducible benefits for a given crystallization system of interest. The features giving a specific range of surface energies for a heterogeneous substrate may comprise arrays of ridges, channels, steps, kinks, terraces, and the like, or any combination thereof, capable of enhancing the coalescence and growth of solutes and solute aggregates of different chemical characteristics and physical properties, including different sizes or shapes. The size and shape variability afforded by the arrays for surface energy modification of the subject invention is another key differentiating feature, as the current state of art relies principally on epitaxial-inspired methods with rigid templates and narrowly defined lattice energies ($E_{latt}$). By creating a means of enhancing solute aggregation and predisposing these solute aggregates to secondary coalescence (i.e., aggregation of aggregates) to facilitate growth to the critical size needed to nucleation, the subject invention can be used to rationally effect improvements to nucleation thermodynamics, nucleation kinetics, crystal growth thermodynamics, crystal growth kinetics, crystal morphology, crystal size distribution, ease of processing, isolation of thermodynamically favorable crystalline forms, and the like.

The ability to conveniently, cost effectively, and reproducibly create heterogeneous amorphous substrates with different surface energies using chemical, spectroscopic, radiation, thermal, or lithographic means, or by melting, stamping, imprinting, printing additively, or other such manufacturing methods practiced by those skilled in the art, is one important advantage supporting broad utility of the subject invention. Broad variation in surface functionalization and, hence surface energies, affords one means of tuning the substrate surface energetics to suitably match the energetics preferred by a given solute in a supersaturated solution. By providing a substrate surface with an advantageous energy range, there is a higher probability of obtaining a match between the solute attachment energy ($E_{att}$) and the surface energy of the substrate surface. It is this range in energies, or the energetic window, that expands the utility of the subject invention well beyond the narrowly defined energetics and usefulness of secondary nucleation methods, including the specific case of liquid phase epitaxy.

In addition to the spatial variation of the nucleation sites, whether present as ridges, channels, or the like as may be contemplated, some degree of orientational variation will permit accommodation of aggregates of different size, shape, or chemical identity. This positional variability affects the surface energy of a given amorphous substrate and provides another means of accommodating solute and system energetics without enforcing a narrow energetic regime defined by a preexisting lattice.

It is anticipated that the heterogeneous substrate surface features can contain comparatively sharp edges and features (e.g., crenels) as might be encountered on a growing crystal surface having defined lattice angles and morphology, or rounded edges (e.g., dimples) as might be more accommodative of aggregates in a solution, or combinations thereof, that might be advantageous for a given system. In any case, it is the net effect of a surface energy modification and the impact of this energy change on the nucleation process that is one important aspect of the subject invention.

The present invention employs a substrate as a cost effective, physical support that is resistant to dissolution during use. Suitable substrates include, but are not limited to, polypropylene, polyethylene, polytetrafluoroethylene, polyacrylate, polyacrylamide, polystyrene, divinylbenzene, vinylbenzene, copolymers of the aforementioned materials, glass, and other amorphous materials that may be used by those familiar in the art. This list includes, and is selected from, materials that are generally resistant to chemical reaction in traditional laboratory and production-scale solutions from which crystallization may be performed. These materials may be employed as the bulk, as surface layers adhered to another surface, and in other combinations as may be advantageous to positively affect nucleation, crystal growth, or both.

The subject invention may be utilized in any of the following formats, and these are presented as examples and are not intended to be limiting in any way. The amorphous heterogeneous substrates may be used as a containment vessel, as a surface in contact with a solution that is, or becomes, supersaturated, as by a module adhered to or incorporated into a container wall, or as a freely floating or suspended module below, at, or in intermittent contact with a solid, liquid, or gaseous interface of a solution. More specifically, the aforementioned interface with a solution may include any of the following, alone or in combination: an air/liquid interface, a gas/liquid interface, a solid/liquid interface, and another liquid/liquid interface. The amorphous heterogeneous substrate may be selected from a class of amorphous organic polymers, copolymers, or inorganic materials that are generally chemically resistant to dissolution or passivation by a contemplated supersaturated solution so that dissolution equilibria and contaminants that may interfere with nucleation and crystal growth processes are minimized. The amorphous heterogeneous substrates generally represent commodity materials readily available at low cost and have the properties of durability, flexibility, and resistance to dissolution. As an amorphous material, the likelihood of system shear forces causing substrate fracture leading to a change from heterogeneous primary nucleation to a secondary nucleation method are eliminated, as the substrate materials in contact with the solution are noncrystalline. These characteristics overcome many of the disadvantages encountered by epitaxial-style growth from solution and other systems where secondary nucleation mechanisms are involved.

Particularly preferred materials may also be selected from the class of amorphous materials that are thermally stable with respect to temperature changes. Given the well established effects of temperature on S (Eqn. 1), as described herein, it is advantageous to concurrently use the modified nucleation surfaces of the subject invention with a means of lowering, raising, or alternatively cycling the temperature of a system for which nucleation and crystal growth is desired. The net effect of the temperature modulation could be a bulk change to solution temperature, or it could be a thermal perturbation to a microdomain of the solution. Because supersaturation is a nonequilibrium condition and the effects of microdomain temperature changes on nucleation and crystal growth are not fully understood, a minor thermal perturbation in proximity to a contemplated modified nucleation surface may produce a value of S and an energetic regime that suitably overcomes the activation barrier to nucleation for a given solute system. Methods of changing the system temperature, whether in the macroscopic or the microscopic domain, are well known in the art, including, but not limited to, fluid jacketed vessels, heating elements, cold fingers, recirculating refrigerants, recirculating hot fluids, thermoelectric devices, cryogenic solids and liquids, and the like as may be contemplated.

Additional particularly preferred amorphous substrate materials may derive from the class of biocompatible polymers or amorphous inorganic materials, and such materials are important in bioengineering applications. By example, hydroxyapatite is the principal component of bones and teeth and is formulated as $Ca_{10}(PO_4)_6(OH)_2$. The process by which hydroxyapatite is deposited in biological systems is termed biomineralization, and the mechanism involves heterogeneous nucleation and subsequent crystal growth of hydroxyapatite on energetically favorable biological surfaces. The process of implant fixation and integration into the surrounding tissues is known as osseointegration, and it is integral to promoting both function and longevity of the implant. The incorporation (e.g., through coating or other techniques) of hydroxyapatite into the surface of engineered implantation materials may be beneficial to the osseointegration process. Unfortunately, ex-vivo attempts at the nucleation and crystallization of hydroxyapatite using in-vivo conditions (i.e., aqueous conditions, atmospheric pressure, and physiological temperature) result in nanometer sized crystals that are approximately 10- to 100-fold smaller than the micrometer size obtained in biomineralization. The crystals derived ex vivo are of such a small size that they fail to impart the beneficial attributes of the larger hydroxyapatite crystals produced in vivo through native biomineralization. In view of this need, the modified surfaces of the subject invention are useful in such bioengineering applications as the nucleation surfaces of the subject invention are of utility in promoting the growth of appropriately sized hydroxyapatite crystals.

An important advantage of surface modification of amorphous materials to improve heterogeneous nucleation is that the probability of formation of an aggregate of appropriate size for nucleation is improved by use of a comparatively broad surface energy spectrum rather than by use of the characteristically narrow energy spectrum of crystalline substrates, as shown in FIG. 5. The approach of the subject invention also leaves intact the chemical recognition and assembly processes important to aggregate formation, aggregate growth, nucleation, and crystal growth, rather than surrogating the recognition and related assembly processes with the rigid energetic template of a crystalline substrate that may not be an appropriate thermodynamic match for the target solute.

By strategically optimizing the surface energy, motif, and nucleation site density, it has been demonstrated in the subject invention that the effects of contaminant related heterogeneous primary nucleation can be reduced. The breadth of processes and facilities involved in modern crystallization processes means chemical impurities and particulate contaminants cannot be entirely eliminated. The subject invention seeks to statistically reduce the likelihood and impact of these contaminant breaches by optimizing the nucleation site density of an amorphous heterogeneous surface for a given crystallization system. More generally, the predominance of contaminant related heterogeneous primary nucleation by dust particle surfaces and the like is attributable to the reduced energetic barrier to nucleation presented by the contaminant surface. Such contaminant induced nucleation lacks the predictable behavior needed by a new technological tool, and the use of modified amorphous surfaces with a tuned surface energy spectrum presents a more predictable approach. By reducing the activation barrier to nucleation in a controlled manner using engineered nucleation sites present in numbers that exceed the contaminant, the probability of contaminant induced nucleation is minimized. Such an approach would have a favorable effect on process quality, predictability, and economics.

EXAMPLES

These examples are provided for illustrative purposes only and not to limit the scope of the claims provided herein.

The term "surface modification" used herein is defined to include any change to the substrate as by physical, chemical, or other means that may introduce a topographic feature or features that results in a perturbation to the substrate surface energy when in contact with a solution. Surface modifications were made on soda-lime glass microscope slides (Karter Scientific Microscope slides P/N 206A2, 1.0+0.2 mm thickness, pre-cleaned) with a Trotec Speedy 300 $CO_2$ laser system. Exemplary surface modification templates were prepared using CorelDraw X6 Software (Corel, Inc.) using a line weight of 0.35 point (25.4 mm/72 points×0.35 point≈120 mm). The laser settings employed a resolution of 1000 dots per inch (dpi) and a 30% laser head speed.

Figure 6:
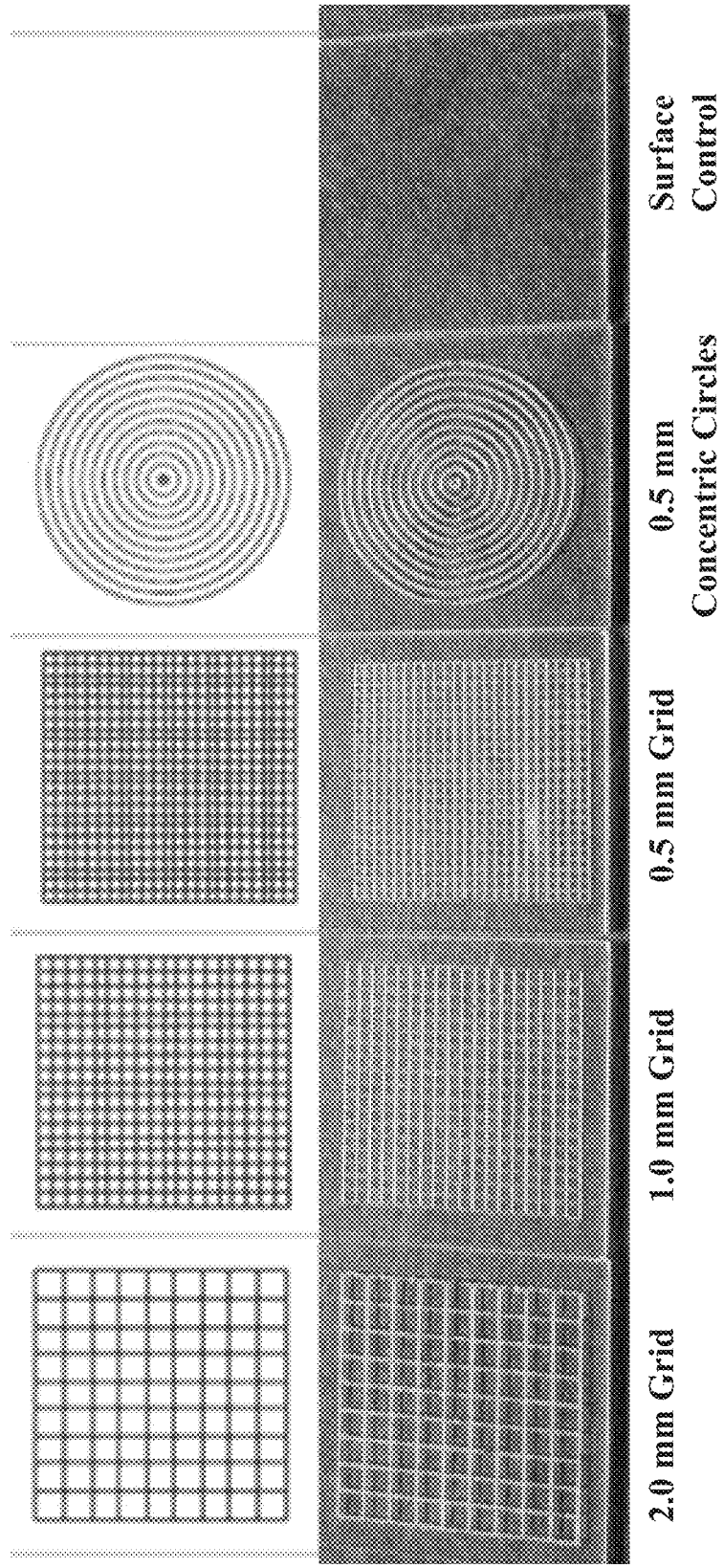
FIG. 6. Exemplary nucleation motifs (top row) used in the subject invention and their physical appearance on an amorphous substrate (bottom row).

Exemplary motifs for surface modification are shown in FIG. 6, and these examples are intended for illustrative purposes only and not intended to be limiting in any way. The amorphous Si surfaces with the modifications shown in FIG. 6 were used in the Examples described herein. Three square grid patterns with plateaus of 2.0 mm 1.0 mm, and 0.5 mm were manufactured, as was a surface containing a series of concentric circles. The motifs labeled 0.5 mm Grid and 0.5 mm Circles were engineered to have comparable contact ratios with a drop: specifically the peak to valley surface area contact ratio was arbitrarily targeted to a ratio of approximately 5.7. This was defined by the grid, and then accomplished for the concentric circles by assigning an identical linewidth and then reducing the outside diameter of the initial 20 mm circle by approximately 8.75% for each smaller circle. In this way, a direct comparison between the effects of a crenellated grid and crenellated circular surfaces on a sessile drop could be obtained, as the plateau/valley surface area ratios are comparable at approximately 5.7.

Example 1

Contact Angle Measurements

Contact angle measurements (Lamour, G. and Hamraoui, A., Contact Angle Measurements Using a Simplified Experimental Setup. *J. Chem. Educ.* 2010, 87(12), 1403-1407) are used to evaluate surface treatments in many fields including surface chemistry and biomaterials. An understanding of the macroscopic properties of surface energy and wettability is useful for the modified and unmodified nucleation surfaces to be used for nucleation and crystal growth. We employed the sessile drop technique for the measurement of contact angles, which is generally accepted as described in the literature.

A drop of pure liquid on a plane solid surface experiences adhesive forces acting between the liquid and the solid surface that favor spreading, whereas the cohesive forces within the liquid counteract this spreading. A substrate with a surface energy that is higher than the surface tension of a liquid drop will undergo complete wetting so that interactions between the liquid and substrate dominate, resulting in a contact angle of 0°. If the substrate has an intermediate surface energy that is below that of the surface tension of the liquid, the liquid will wet the substrate and the contact angle will be in the range of 0°<θ<90°. If the substrate has a surface energy that is substantially lower than that of the surface tension of a liquid drop, the surface is said to be non-wetting (or poorly wetting) resulting in contact angles for water in excess of 90°.

The contact angle experiments described below target an understanding of the comparative contact angles between modified and unmodified substrate surfaces. Because the modified surface features are larger than the sessile drops used in these measurements, a non-equilibrium, dynamic contact angle can be expected due to the drop spreading on the substrate surface. The experimental protocol for the measurement of contact angles for sessile drops has been described in the literature. Briefly, the topographically patterned and non-patterned slides are placed on a level aluminum block inside a photographic light chamber. A 20 μL drop of $H_2O$ from a 25 μL gas tight syringe (Hamilton Model #1702) was then positioned directly on the center of each of the modified- or unmodified surfaces (the latter henceforth referred to as the surface control) shown in FIG. 6, followed by image acquisition via digital photography. Contact angle measurements were conducted at ambient temperature ($\approx$20° C.). In order to facilitate adequate image contrast, the drop was back-light illuminated using a 50 W halogen lamp shone through a paper diffuser housed inside the photographic light chamber. Photographic image data was collected every 15 min over the course of 1 h through a dedicated camera monocular on an Amscope 3.5-90× Trinocular Zoom Stereo Microscope using a Canon EOS Rebel T2i digital 18 Megapixel camera equipped with a Fotodiox D-SLR Camera Adapter (2× magnification). The microscope and camera were positioned at 90° incident to the interface of the substrate surface with the sessile drop with the aid of a telescoping 3D boom stand. The field of view was adjusted via magnification in order to achieve adequate image size for processing and was approximately 4× through the camera lens. The resulting photographic images were then analyzed with the ImageJ software (Version 1.46, National Institutes of Health) using the contact angle software module plug-in to determine the angle of contact for each sessile drop. Contact angle curve fitting employed manual point selection in conjunction with the ellipsoid curve "best fit" feature of the software.

As shown in Table 1, the four modified surfaces show steady decreases in contact angle for sessile $H_2O$ drops as a function of time. By contrast to the modified surfaces of the slides, contact angles for drops deposited on the surface control exhibited only a slight decrease in contact angle ($\approx$6°) within the first 15 min of measurement, after which the contact angles remained essentially unchanged at θ$\approx$15°. Complete wetting (i.e., θ, $\approx$0°) was observed for both the 0.5 mm and 1.0 mm grid modifications, meaning that the surface energies of these modifications exceed the surface tension of $H_2O$ itself, which is 72.8 mN/m. By inference, the 2.0 mm Grid surface with a contact angle of 3.6° at 1 h has a surface energy only slightly lower than that of water, while the circular motif has the lowest surface energy of the four modified surfaces and can be estimated from the contact angles at approximately 50% that of that of the surface control.

TABLE 1

Dynamic contact angle measurements on modified and unmodified substrate surfaces at 20° C.

| | Surface Modification | | | | |
| --- | --- | --- | --- | --- | --- |
| Time (h) | 0.5 mm Grid Contact Angle | 1.0 mm Grid Contact Angle | 2.0 mm Grid Contact Angle | 0.5 mm Conc. Circles Contact Angle | Surface Control Contact Angle |
| 0.00 | 32.6 | 22.5 | 25.7 | 30.0 | 20.8 |
| 0.25 | 24.0 | 20.1 | 23.3 | 26.5 | 14.8 |
| 0.50 | 9.7 | 12.8 | 20.0 | 18.0 | 15.3 |
| 0.75 | 2.5 | 3.1 | 14.1 | 12.2 | 14.8 |
| 1.00 | $\approx$0 | $\approx$0 | 3.6 | 7.2 | 13.9 |
| Rate of Change (degrees/h) | 32.6 | 22.5 | 22.1 | 22.8 | 6.9 |

During and after the course contact angle experiments comparable to those described here, it was observed that the $H_2O$ drops remain comparatively strongly adhered to the modified surfaces such that the substrates could be tilted without substantial movement of the drop. For the grid patterns exhibiting the most effective wetting and lowest contact angles, the substrates themselves could be completely inverted without the drop moving to an edge or running off the surface. This observation could be advantageous, for example, in situations where a drop of a supersaturated solution is required to be inverted (i.e., hang) for analytical investigations, solvent diffusion, or crystal growth purposes.

Example 2

Evaporative Mass Losses

Evaporation is a very common method of increasing both the solute concentration and S (the supersaturation ratio) to induce nucleation. The total mass of material is frequently limited at the discovery phase for a new chemical entity, and it is common practice for small volumes of solution to be slowly evaporated from loosely capped culture tubes, vials, and the like, to gradually increase the supersaturation ratio (S, Eqn. 1) and induce crystallization. Hanging drop, and the related sessile drop methods, are often used in the crystallization of proteins for structure determination and are prized techniques for their ability to produce well-ordered crystalline materials. Hanging and sessile drop methods may also involve vapor phase diffusion of an antisolvent (i.e., another solvent in which the target solute is less soluble) into the drop containing the solute of interest to slowly increase S and thereby induce nucleation. Both evaporative and solvent/antisolvent exchange methods are fundamentally affected by the drop size, drop shape, relative solute solubilities, and other physical factors including temperature, contact angle with the substrate surface, and the surface energy.

In order to study the comparative rates of solvent evaporation from the modified surfaces and control surface of FIG. 6, an analytical balance (Mettler Toledo, Model AX304) was used in a mass-based determination of the rate of evaporation. Surfaces to be examined were placed individually on the analytical balance, tared, and then a 20 μL drop of $H_2O$ was placed on the surface using a 25 μL syringe. Samples were allowed to sit on the balance and mass measurements were taken at 15 min intervals.

Data reporting the rate of evaporation are presented in Table 2. The results generally follow the same patterns as the contact angle measurements; that is, the smallest dynamic contact angle measurements (Table 1) and the rate of evaporation are generally fastest with the grid-based surface modifications. The evaporation rates for the 0.5 mm Circles and the surface control have statistically significant differences (>3 estimated standard deviations (esd)) from the grid motifs and exhibited the slowest mass losses due to evaporation.

TABLE 2

Evaporative mass losses from modified and control surfaces at 20° C.

| Time (h) | 0.5 mm Grid Drop mass (mg) | 1.0 mm Grid Drop mass (mg) | 2.0 mm Grid Drop mass (mg) | 0.5 mm Conc. Circles Drop mass (mg) | Surface Control Drop mass (mg) |
|---|---|---|---|---|---|
| 0.00 | 20.4(4) | 21.5(2)[a] | 19.8(2) | 21.0(1) | 20.4(2)[a] |
| 0.020 (1 min) | 20.0(3) | 21.2(1) | 19.6(2) | 20.8(2) | 20.2(2)[a] |
| 0.25 | 16.4(6) | 17.8(1) | 16.4(2) | 18.4(4) | 17.8(5) |
| 0.50 | 12.8(4) | 14.2(1) | 13.1(2) | 15.9(6) | 15.2(1) |
| 0.75 | 9.2(5) | 11.0(6) | 9.8(2) | 13.4(5) | 12.4(1) |
| 1.00 | 5.5(3) | 7.6(6) | 6.6(1) | 10.8(6) | 9.5(2) |
| Rate of change (mg/h) | 14.9(5) | 13.9(6) | 13.2(2) | 10.2(6) | 10.9(3) |

[a]Replicate experiments were not performed for these measurements. The reported estimated standard deviations are averages calculated from measurements at the same time increment (i.e., same row). These data are used in the Evaporative Rate of Change calculations.

As discussed elsewhere, the extent of drop spreading depends on the surface energy of the solid and on the surface tension of the liquid (Cazabat, A. M., Cohen-Stuartt, M. A. *J. Phys. Chem.* 1986, 90, 5845-5849). A given drop spreads, or alternatively decreases its contact angle, more effectively on the grid modified amorphous surfaces because the drop is afforded a different energy profile and more degrees of freedom with respect to travel along intersecting channels. Because the drop flattens and becomes larger on the grid modified surfaces, the drop features change and the overall drop height and size can lead to accelerated evaporation.

The surface control has no channels and the $H_2O$ drop remains pinned because the surface energy of the slide is less than the viscosity of the water. The 0.5 mm Circles present an interesting hybrid between the grid motifs and the control surface in that the degrees of freedom are limited as the channels comprising the concentric circles are not in flow contact with one another. The contact angles at 1 h and the dynamic contact angle rate of change for the 0.5 mm Circles suggest surface energies and evaporative behavior resembling more the grid modified surfaces; however, the evaporative data and the propagated errors suggest a statistically significant closer resemblance to the control surface. The absence of flow communication between the concentric circles and the poorly understood effects of pinning behavior make this a novel finding, as control of evaporation and solvent diffusion techniques to adjust S and to induce nucleation and crystal growth is of utility.

Example 3

Nucleation Site Density and Crystal Size Distribution

A 100 mg/mL aqueous solution of sodium borate decahydrate was prepared by adding 24 g of $Na_2B_4O_7 \cdot 10H_2O$ (Henkel AG) to 240 mL $H_2O$ and subsequently heating to boiling to ensure complete dissolution. The hot solution was then passed through a paper filter and aliquoted for use in nucleation and crystallization experiments.

Six experiments were performed comprising the solvent control, surface control, 2.0 mm Grid, 1.0 mm Grid, 0.5 mm Grid, and 0.5 mm Circle motifs. Approximately 40 mL of hot 100 mg/mL aqueous $Na_2B_4O_7 \cdot 10H_2O$ was added to each capped vessel and (where appropriate) one of the modified nucleation surfaces was inserted so that any motif was completely immersed in the solution. Each nucleation surface was oriented slightly down-facing at an angle of approximately 60-70° to prevent accumulation of solids from any bulk crystallization from solution by the nucleation surface. Vessels were immediately capped and allowed to cool to 20° C. After 0.5 h, small crystals of $Na_2B_4O_7 \cdot 10H_2O$ formed on all engineered motifs shown in FIG. 6, including the surface control. One large crystal formed after approximately 3 h in the solvent control experiment (i.e., no added nucleation surface), and none of the modified nucleation surfaces gave comparably large crystals out to a time of 24 h.

Figure 7:
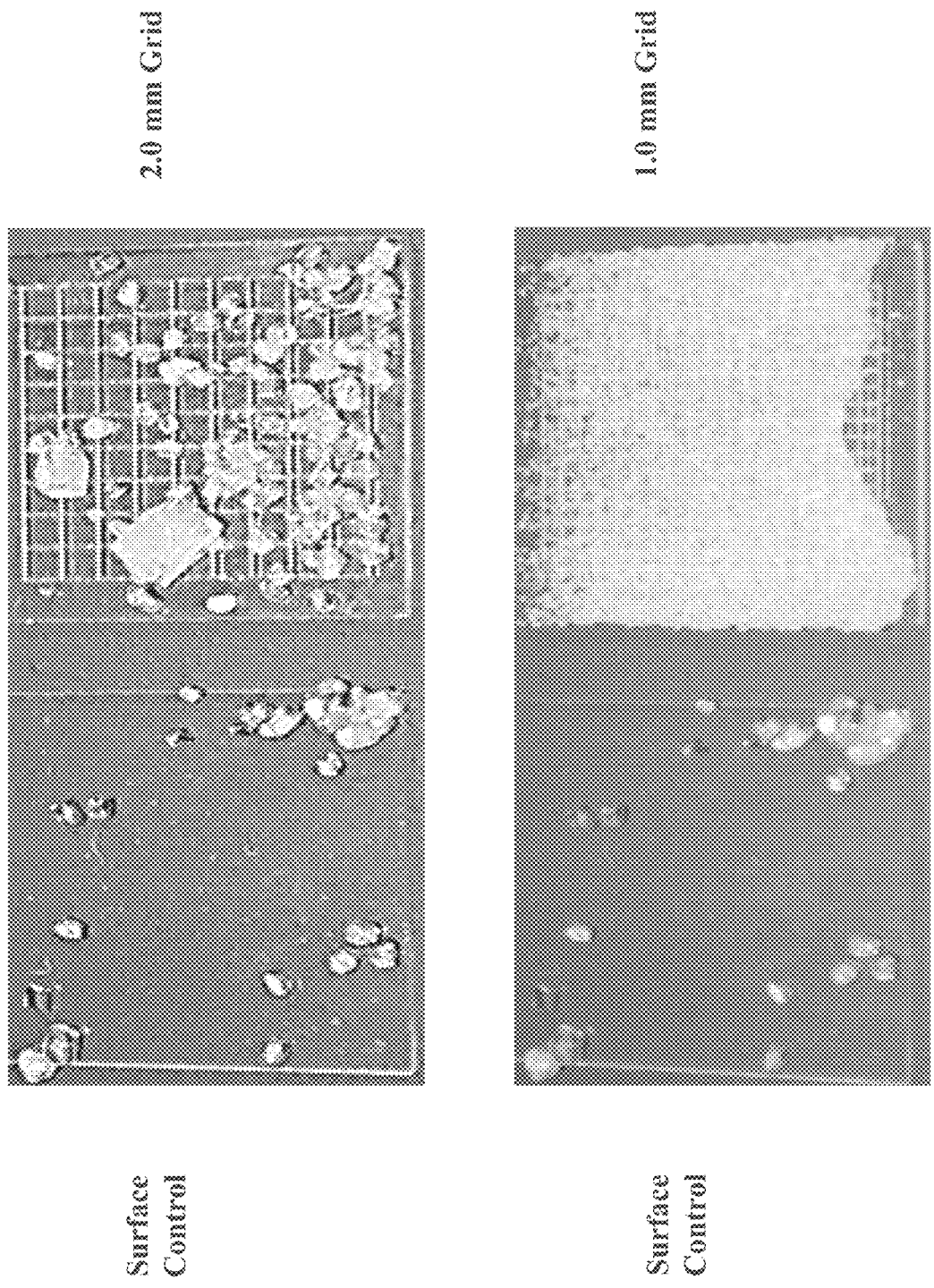
FIG. 7. Nucleation density and crystal size distribution results for the $Na_2B_4O_7 \cdot 10H_2O$ system.
Figure 7:
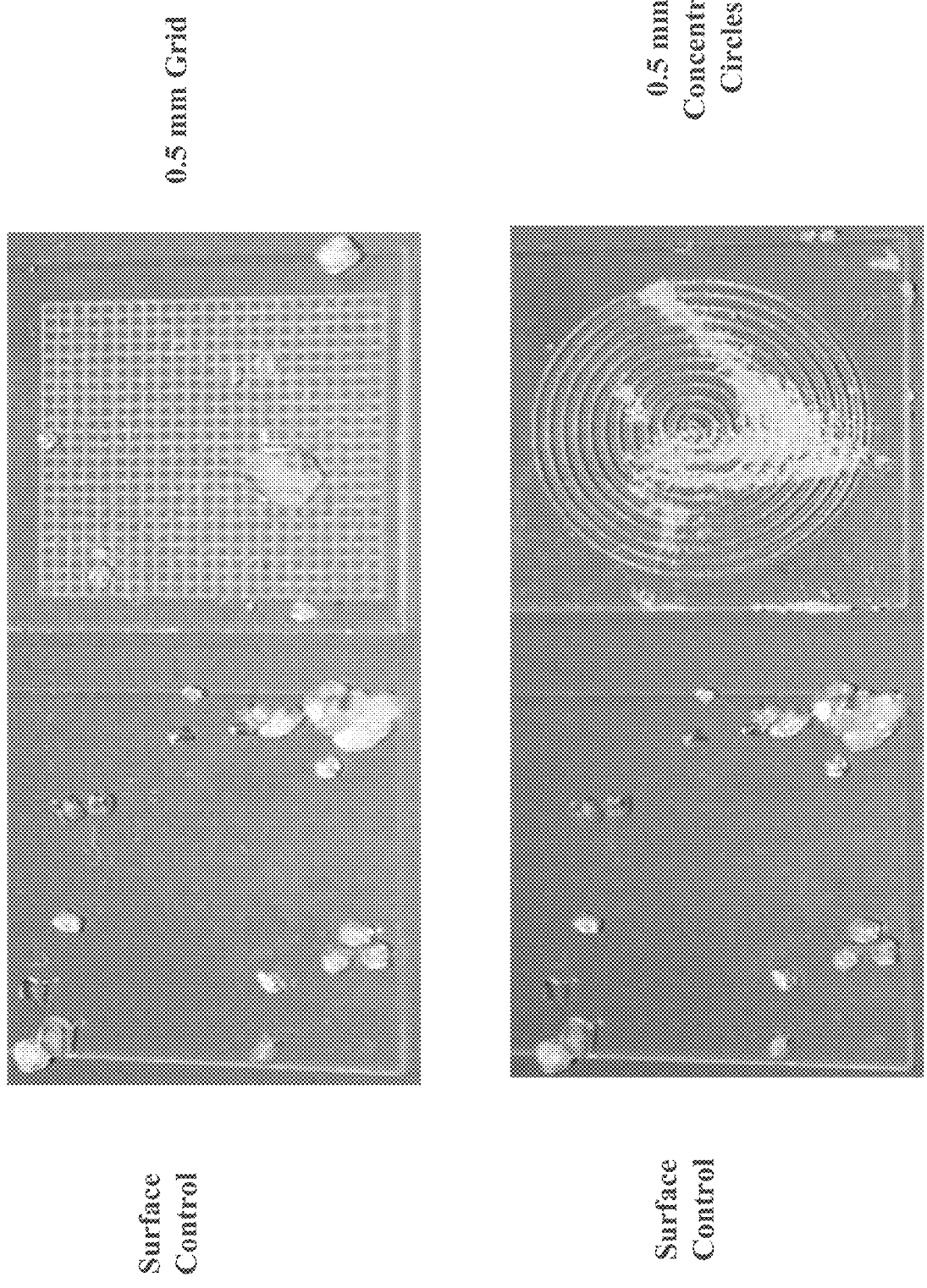

FIG. 7 shows the results of the $Na_2B_4O_7 \cdot 10H_2O$ nucleation and crystallization studies, in which the left column shows the surface control and the right column the crystalline materials that formed on the various modified nucleation surfaces, despite their down-facing orientation. This observation suggests that the nucleation events for $Na_2B_4O_7 \cdot 10H_2O$ occurred on or near the nucleation surfaces, although crystal growth on the subject nucleation surfaces is not required to promote or inhibit nucleation as demonstrated in later examples. The four modified nucleation surfaces of the subject invention clearly exhibit behavior different from the surface control and different from one another. The 2.0 mm Grid motif exhibits a large crystal size distribution, with solids ranging from small microcrystals to larger crystals of approximately 4-5 mm in size. By comparison, the 1.0 mm Grid motif gives a narrow crystal size distribution with microcrystalline solids covering the majority of the modified surface and giving it an opaque appearance due to the reflection of light from the multiple $Na_2B_4O_7 \cdot 10H_2O$ crystals in different orientations.

The 0.5 mm Grid surface gives only a few crystals, with a crystal size distribution similar to that of the 2.0 mm Grid, but with a far lower particle (i.e., crystal) count. The surface coverage of microcrystalline materials on the 0.5 mm Circles is quite low, and the crystal size distribution for the 0.5 mm Circles is similar to the 1.0 mm Grid, despite the absence of 90° intersections in the former.

The large number of microcrystalline solids on the 1.0 mm Grid motif relative to all other surfaces suggests a favorable surface energy for nucleation. More specifically, the large number of microcrystalline solids on the surface of the 1.0 mm Grid very likely reflects a high density of energetically favorable nucleation sites. The 0.5 mm Grid has the most engineered features per unit area and, thus, the highest engineered density of potential nucleation sites; however, FIG. 7 shows that the crystals obtained for the 0.5 mm Grid more closely resemble the sizes, shapes, and size distribution obtained using the 2.0 mm Grid and control surfaces. Thus, it is not merely the number of engineered nucleation sites, rather there must be an appropriate match between the surface energy of the modified nucleation surface and $E_{att}$ (Eqn. 9) of the solute of interest.

Several key points regarding utility can be drawn from FIG. 7; specifically, that the 1.0 mm Grid motif is useful in forming small crystals with a narrow crystal size distribution, which may be advantageous for a process that requires rapid dissolution over a narrow timeframe. Alternatively, the 0.5 mm Grid motif is of utility if nucleation and crystal growth were less desirable in a given location. Such a situation may arise in applications involving bioengineering in which implanted surfaces may need to suppress biomineralization or ossification in certain areas and promote it in other regions of the implant. The comparatively broad crystal size distribution of the 2.0 mm Grid surface modification could be useful under various circumstances where particles of different sizes and surface areas find utility, as in; for example, agricultural or food additives in which extended dissolution of mineral or sweetener, respectively, components may be advantageous.

Example 4

Evaporative Crystallization of Acetylsalicylic Acid on Nucleation Surfaces

Figure 8:
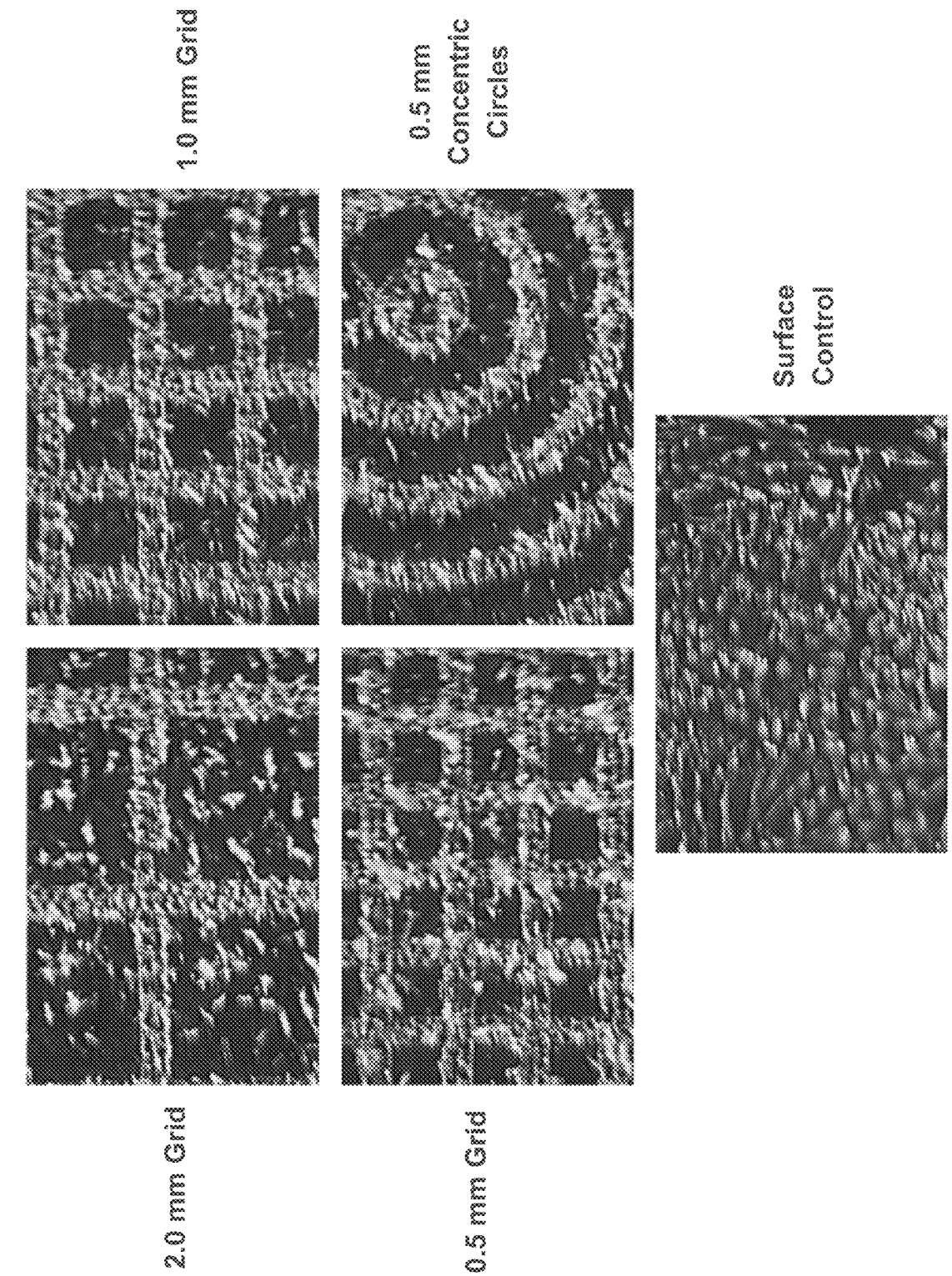
FIG. 8. Localization of nucleation and crystal growth of acetylsalicylic acid on engineered nucleation surfaces and the random behavior of the control surface.

In an unconfined evaporation experiment, 20 μL of a 150 mg/mL solution of acetylsalicylic acid in 91% isopropyl alcohol was delivered onto one each of the modified nucleation surfaces and onto a corresponding surface control. Each solution was allowed to evaporate at room 20° C. After complete evaporation, the resulting crystals were examined under a stereomicroscope with approximately 2× magnification, as shown in FIG. 8. The results show nucleation and crystal growth primarily along and inside the motif features with comparatively fewer crystals nucleating in the unmodified surface regions. The 0.5 mm Circle exhibited more needle-like crystals along the circular motif than the other engineered features. The 0.5 mm Grid pattern also had clustered needle-like crystals in the features with fewer thin needle-like crystals in the pristine surface. The 1.0 mm Grid motif gave shorter acetylsalicylic acid crystals than observed for the other motifs. The surface control gave many random points of nucleation and the acetylsalicylic acid crystals had irregular, starburst-like morphologies.

The images of FIG. 8, obtained via microscopy, provide a glimpse of the relative concentration of crystals, and by extension nucleation sites, in the features of the surface energy modification. These data demonstrate the effectiveness of surface energy modifications with respect to nucleation and crystal growth, as the increased particle density in the motif features is evident and well organized compared to the immediately adjacent surfaces that have not been engineered to contain nucleation sites.

Example 5

Particle Count for Crystals on Modified Nucleation Surfaces

The experiments of Example 4 and FIG. 8 were investigated using the Analyze Particles function of the ImageJ Software (Version 1.46, National Institutes of Health). The software was unable to precisely differentiate between motif features and the large number of acetylsalicylic acid crystals in the features, so the data presented here are for the particle counts in the dark plateau regions of the modified surfaces shown in FIG. 8. In essence, these data reflect the effect of the engineered nucleation sites competing with, and effectively reducing, the random nucleation events of the unmodified surface.

As shown in Table 3, the 0.5 mm Circle motif had fewer acetylsalicylic acid crystals present per unit area of the unmodified region than the rest of the motifs. The 2.0 mm Grid also had a smaller number of acetylsalicylic acid crystals/mm$^2$ on average for the surface area, but this is likely because the crystals formed on this pattern are larger in size than those obtained for the other nucleation surfaces. The 0.5 mm Grid pattern has the most crystals on average for the surface area, but this is due to a smaller crystal size distribution for this motif. Visual inspection of FIG. 8 provides clear evidence that more nucleation and crystal growth occurs in the surface modifications of the 0.5 mm Circle motif than any of the other slides and the 2.0 mm Grid motif had the most crystal growth on the square regions outside the surface features.

TABLE 3

Particle counts from ImageJ software for acetylsalicylic acid on engineered nucleation surfaces.

|  | 0.5 mm Grid | 1.0 mm Grid | 2.0 mm Grid | 0.5 mm Conc. Circles |
|---|---|---|---|---|
| Area Surveyed | 4 mm$^2$ | 16 mm$^2$ | 64 mm$^2$ | Four 0.5 mm circles |
| Particle Count | 117(20) | 150(51) | 252(66) | 43(34) |
| Particles/mm$^2$ | 29(5) | 9(3) | 4(1) | 3(3) |

Example 6

Measurements of Nucleation and Crystallization Times for Modified and Control Surfaces Studies of crystallization times using acetylsalicylic acid as a model system are a standard in the scientific literature to characterize nucleation properties of new materials, and the data presented here followed a locally modified protocol. A 150 mg/mL solution of acetylsalicylic acid (Sigma Aldrich) in 91% (v/v) isopropyl alcohol (Aaron Industries, Inc.) was prepared by combining 37.5 g acetylsalicylic acid with 250 mL 91% isopropyl alcohol and heating to 60° C. in a sealed container to facilitate dissolution. The transparent solution was allowed to cool to ≈20° C. for at least 30 min prior to use and was stable with respect to crystallization at ambient temperatures.

The modified nucleation and control surfaces shown in FIG. 6 were cleaned prior to use by rinsing with 91% isopropyl alcohol and then soaking at 60° C. in 91% isopropyl alcohol for approximately 30 min, after which this solution was discarded. The surfaces were subsequently soaked in H$_2$O at 60° C. for approximately 30 min, rinsed with fresh H$_2$O, and dried upright at 60° C. in a loosely covered container to minimize dust intrusion.

Because of the stochastic nature of crystallization, replicate measurements are necessary and a statistical analysis is an important part of the conclusions drawn from the data. Further, the ubiquitous factors that can induce nucleation and affect crystal growth such as impurities, dust, and the like, require careful manipulations and careful design of the control experiments. Solvent controls (i.e., no nucleation surface present) permit monitoring of solution phase variables; for example, impurities, adventitious solids, and microscopic crystalline fragments, that could induce primary or secondary nucleation and are needed to factor out nucleation events arising from other surfaces competing with the engineered nucleation surfaces of the subject invention. Surface control experiments are also important, as the unmodified regions surrounding the surface modifications may impact the nucleation and crystallization outcomes. In these studies, both the surface control and solvent control experiments were randomized across different solutions to reduce the effect of random errors. This approach involving careful control of solution handling, solvent controls, surface controls, replicate experiments, and statistical analyses gives the highest probability of uncovering statistically significant and reproducible findings.

Crystallization time experiments were performed in 120 mL capped vials to which approximately 40 mL of 150 mg/mL acetylsalicylic acid in 91% isopropyl alcohol had been added. One of the nucleation surfaces was inserted into each vial such that the modified nucleation surface (if present) was completely immersed in the solution. Each surface was oriented slightly down-facing at an angle of approximately 60-70° so that any bulk crystallization from solution would not collect on the nucleation surface. Vials were immediately quenched to 0° C. in an ice/$H_2O$ bath maintained inside a refrigerator at approximately 35° C. Vials were monitored for the appearance of crystalline material at 15 min intervals up to the first 180 min, and less frequently thereafter up to times of 24 h. The onset time of crystallization signaled the end point for a given experiment, and a total of six replicates were performed.

The average crystallization times with estimated standard deviation (esd) for acetylsalicylic acid in 91% isopropyl alcohol at 0° C. are reported in Table 4.

TABLE 4

Average crystallization times (minutes) for acetylsalicylic acid in 91% isopropyl alcohol at 0° C. for control systems and modified nucleation surfaces.

| N = 6 | Solvent Control | Surface Control | 2.0 mm Grid | 1.0 mm Grid | 0.5 mm Grid | 0.5 mm Circles |
|---|---|---|---|---|---|---|
| Avg | No cryst. to 242 | 118 | 40 | 65 | 45 | 60 |
| esd | No cryst. to 242 | 91 | 11 | 33 | 27 | 34 |

Avg. All Surfaces 65
esd All Surfaces 28
Avg Modified Surfaces 52
esd Modified Surfaces 10

The first key finding is that none of the solvent control experiments exhibited spontaneous nucleation and crystallization to a time of 242 min, and many were stable for over 24 h. The lack of crystallization by these solvent control experiments are indications of system stability and experimental care to preclude dust, dander, and particulates that can serve as adventitious nucleation surfaces. For each of the modified nucleation surfaces and for the control surface, acetylsalicylic acid crystals were first observed floating at the air/solution interface and later crystals frequently settled from solution onto the bottom of the reaction vial.

The surface control data yields an average time to crystallization of 118 min with an esd of 91 min: 118(91) min. The surface control is "unmodified", while presenting to the control solution a bulk surface and edge features that are common to all experiments (excluding the solvent control). The range in surface control crystallization times from 29.5-242.0 min gives a large esd of 91 min, which is a statistical representation of poor reproducibility in crystallization by the unmodified surface.

Averaging the crystallization times for all five surfaces, including the surface control, gives a value of 65(28) min. To determine if the engineered surfaces are effecting a statistically significant reduction in nucleation and crystallization times, one takes twice the esd of 28 min for this average and looks for crystallization times that are 2 esd different for a 95.5% confidence level. By example, any crystallization times that are 2*28=56 min or more different from the surface control value of 118(91) min are statistically different at the 95.5% confidence level (i.e., 118−(2*28)=62 min or less). Using this standard approach, the 2.0 mm Grid, 0.5 mm Grid, and 0.5 mm Circle modified surfaces all meet the statistical criteria, and the 1.0 mm Grid motif surface is very close to the 2 esd low end cut off value of 62 min.

The statistical analysis above permits the separation of the 2.0 mm Grid, 1.0 mm Grid, 0.5 mm Grid, and 0.5 mm Circle motifs of the subject invention from the surface control data, and the average crystallization time for these four modified surfaces is 52(10) min. Comparing this value with that of the surface control permits two important observations that relate directly to the utility of the subject invention: (1) a 56% reduction in onset time to nucleation and crystallization by the surfaces of the subject invention compared to the surface control is novel and of utility in time sensitive crystallization operations, and (2) a 9.1-fold improvement in time consistency (calculated by dividing the esd of the surface control by the esd of the average for the modified surfaces: 91/10=9.1) is a notable improvement in reproducibility, and the economic advantages of predictability in business and production operations are well established.

From the foregoing it will be observed that numerous modifications and variations can be effectuated without departing from the true spirit and scope of the novel concepts of the invention. It is to be understood that no limitation with respect to the specific embodiments illustrated is intended or should be inferred. The disclosure is intended to cover by the appended claims all such modifications as fall within the scope of the claims.

Each of the patents, applications and articles cited herein is incorporated by reference. The use of the article "a" or "an" is intended to include one or more.

What is claimed:

1. A process of initiating nucleation of crystals of a solute from a solution of the solute, or for generating crystalline material of a solute from a solution of the solute, or combinations thereof comprising contacting the solution of the solute with a substrate having an amorphous heterogeneous surface, wherein the amorphous heterogeneous surface of the substrate:
   1) incorporates a pre-formed nucleation site array;
   2) is placed in direct contact with a solution comprising the solute to be crystallized under conditions that are static, dynamic, or flow, or combinations thereof;
   and
   3) is chemically resistant to dissolving in the solution.

2. The process of claim 1, wherein the solution of the solute is, or becomes, supersaturated with the solute.

3. The process of claim 1, wherein the process comprises at least one additional step of heating, cooling, or thermally modulating the substrate and the solution of the solute to a temperature that is different from ambient temperature and then heating, cooling, or thermally modulating the solution of the solute and substrate to give a supersaturated solution at a temperature that is equal to, or different from, ambient temperature.

4. The process of claim 1, wherein the process further comprises isolating crystals that are formed by contact of the surface of the substrate with the solution, from the substrate, or the solution, or combinations thereof.

5. The process of claim 1, wherein the pre-formed nucleation site array comprises an array of indentations, dimples, crenels, ridges, channels, steps, kinks, or terraces, or combinations thereof.

6. The process of claim 1, wherein the amorphous heterogeneous surface incorporating the pre-formed nucleation site array modifies the contact angle, line tension, wettability, or surface energy, or combinations thereof, with the solution as compared to the same surface lacking the pre-formed nucleation site array.

7. The process of claim 1, wherein the pre-formed nucleation site array is engineered on the surface by means of manual, mechanical, or chemical methods, or combinations thereof, to engrave, etch, mill, imprint, lithograph, or print additively, or combinations thereof, on the surface.

8. The process of claim 1, wherein the substrate comprises polypropylene, polyethylene, polytetrafluoroethylene, polyacrylate, polyacrylamide, polystyrene, divinylbenzene, or vinylbenzene, or combinations thereof.

9. The process of claim 1, wherein the substrate is a glass substrate.

10. The process of claim 1, wherein the substrate with the amorphous heterogeneous surface is adhered to a second substrate.

11. The process of claim 10, wherein the second substrate is a material that is resistant to dissolving in the solution.

12. A kit comprising a plurality of substrates for generating crystals of a solute from a solution, wherein each substrate:
  1) incorporates a pre-formed nucleation site array on the surface of the substrate;
  2) is placed in direct contact with a solution comprising the solute to be crystallized under conditions that are static, dynamic, or flow, or combinations thereof;
  and
  3) is chemically resistant to dissolving in the solution;
  and wherein each substrate comprises a pre-formed nucleation site array that is identical to, or differs from, other pre-formed nucleation site arrays in the kit.

13. The kit of claim 12, wherein the pre-formed nucleation site arrays on the surface of the substrates comprise an array of indentations, dimples, crenels, ridges, channels, steps, kinks, or terraces, or combinations thereof.

14. The kit of claim 12, wherein the surface of the substrates incorporating the pre-formed nucleation site arrays modifies the contact angle, line tension, wettability, or surface energy, or combinations thereof, with a solution as compared to the same surface lacking the pre-formed nucleation site array.

15. The kit of claim 12, wherein the pre-formed nucleation site array is engineered on the surface by means of manual, mechanical, or chemical methods, or combinations thereof, to engrave, etch, mill, imprint, lithograph, or print additively, or combinations thereof, on the surface.

16. The kit of claim 12, wherein the substrates comprise polypropylene, polyethylene, polytetrafluoroethylene, polyacrylate, polyacrylamide, polystyrene, divinylbenzene, or vinylbenzene, or combinations thereof.

17. The kit of claim 12, wherein the substrates are a glass substrate.

18. The kit of claim 12, wherein the substrates with an amorphous heterogeneous surface are adhered to a second plurality of substrates.

19. The kit of claim 18, wherein the second plurality of substrates are chemically resistant to dissolving in the solution.

20. The kit of claim 12, wherein the kit comprises a means for controlling temperature, or modulating temperature, or combinations thereof.

* * * * *